US012609201B2

(12) United States Patent
Kadoya et al.

(10) Patent No.: US 12,609,201 B2
(45) Date of Patent: Apr. 21, 2026

(54) PROGNOSIS PREDICTION DEVICE, PROGNOSIS PREDICTION METHOD, AND PROGRAM

(71) Applicant: TOHOKU UNIVERSITY, Sendai (JP)

(72) Inventors: Noriyuki Kadoya, Sendai (JP); Mariko Umeda, Sendai (JP); Yuto Sugai, Sendai (JP); Shohei Tanaka, Sendai (JP); Keiichi Jingu, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 279 days.

(21) Appl. No.: 18/551,988

(22) PCT Filed: Mar. 28, 2022

(86) PCT No.: PCT/JP2022/014827
§ 371 (c)(1),
(2) Date: Sep. 22, 2023

(87) PCT Pub. No.: WO2022/210473
PCT Pub. Date: Oct. 6, 2022

(65) Prior Publication Data
US 2024/0177863 A1 May 30, 2024

(30) Foreign Application Priority Data
Mar. 31, 2021 (JP) ................................. 2021-060268

(51) Int. Cl.
G16H 50/20 (2018.01)
G06T 7/00 (2017.01)

(52) U.S. Cl.
CPC ........... G16H 50/20 (2018.01); G06T 7/0012 (2013.01); *G06T 2207/10081* (2013.01);
(Continued)

(58) Field of Classification Search
CPC ......... G06T 7/0012; G06T 2207/30096; G06T 2207/30024; G06T 2207/10056;
(Continued)

(56) References Cited

U.S. PATENT DOCUMENTS

2006/0036372 A1* 2/2006 Yener ................... G06V 20/695
703/11
2010/0111396 A1* 5/2010 Boucheron ............. G06F 18/29
382/133
(Continued)

FOREIGN PATENT DOCUMENTS

CN 110210578 A 9/2019
EP 3611694 2/2020
(Continued)

OTHER PUBLICATIONS

Hosny et al., "Deep learning for lung cancer prognostication: A retrospective multi-cohort radiomics study", PLoS Medicine, vol. 15, No. 11, Nov. 30, 2018, 25 pages.
(Continued)

*Primary Examiner* — Courtney Joan Nelson
(74) *Attorney, Agent, or Firm* — Dority & Manning, P.A.

(57) ABSTRACT

An aspect of the invention is a prognosis prediction device including a prognosis prediction unit that predicts, using prognosis prediction information that indicates a relationship between graph tumor information that is information on an image of a tumor represented using an amount defined by a graph theory and a prognosis of a person or an animal having the tumor, a prognosis of an estimation target based on graph tumor information indicating an image of a tumor of the estimation target.

6 Claims, 15 Drawing Sheets

(52) U.S. Cl.
CPC ............... *G06T 2207/20072* (2013.01); *G06T 2207/20081* (2013.01); *G06T 2207/20084* (2013.01); *G06T 2207/30096* (2013.01)

(58) Field of Classification Search
CPC ........... G06T 2207/20072; G06T 7/162; G06T 2207/30004; G06T 7/00; G06T 7/33; G06T 2210/41; G06T 2207/10081; G06T 2207/2008; G06T 2207/20084; G16H 50/20; G16H 30/40; G16H 30/20; G16H 50/30; G16H 70/60; G16H 30/00; G06V 2201/03; G06V 10/426; G06V 20/69; G06V 10/7635; A61B 2576/00; A61B 1/000094; A61B 8/5207; G06F 18/2323; G06F 18/23
See application file for complete search history.

(56) References Cited

U.S. PATENT DOCUMENTS

| | | | |
|---|---|---|---|
| 2012/0106821 A1 | 5/2012 | Madabhushi et al. | |
| 2015/0213598 A1* | 7/2015 | Madabhushi | G06V 10/758 |
| | | | 382/128 |
| 2015/0254494 A1 | 9/2015 | Madabhushi et al. | |
| 2018/0253591 A1* | 9/2018 | Madabhushi | G06V 20/695 |
| 2018/0253841 A1 | 9/2018 | Madabhushi et al. | |
| 2020/0302603 A1 | 9/2020 | Barnes et al. | |
| 2021/0166387 A1* | 6/2021 | Chatterjea | G06T 7/0012 |

FOREIGN PATENT DOCUMENTS

| | | |
|---|---|---|
| JP | 2008522273 | 6/2008 |
| WO | WO0014668 A1 | 3/2000 |
| WO | WO2006056786 | 6/2006 |
| WO | WO2020067481 | 4/2020 |

OTHER PUBLICATIONS

PCT International Search Report (with English translation) for corresponding PCT Application No. PCT/JP2022/014827, mailed Jun. 21, 2022, 5 pages.

Written Opinion for corresponding PCT Application No. PCT/JP2022/014827, mailed Jun. 21, 2023, 3 pages.

Swedish Office Action for corresponding Application No. 2351110-8, dated Apr. 5, 2024, 8 pages.

Zhou et al, "Novel radiomic features based on graph theory for PET image analysis", IEEE 16th International Symposium on Biomedical Imaging, Venice, Italy, Apr. 2019, p. 1311-1314.

Japanese Office Action (w/English translation) for corresponding Application No. 2021-060268, mailed on Mar. 5, 2025, 6 pages.

Nakamoto et al., "An Introduction to Radiomics: Toward a New Era of Precision Medicine", Japan Society of Medical Physics, vol. 38, No. 3, 2018, 11 pages.

* cited by examiner

FIG. 3

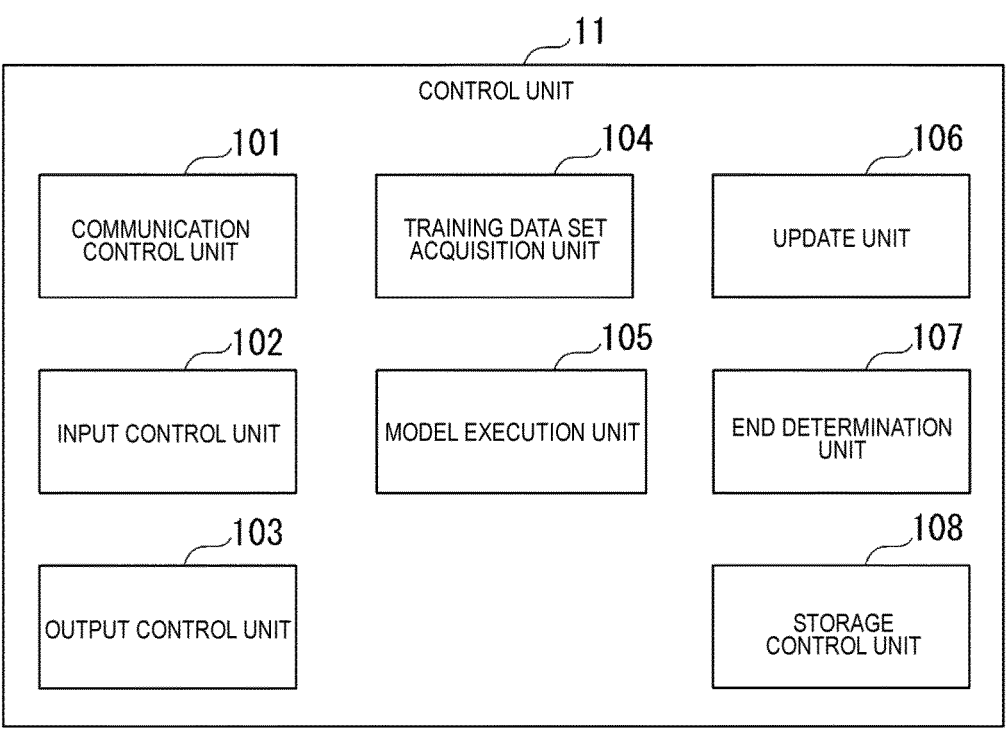

11

CONTROL UNIT

| 101 COMMUNICATION CONTROL UNIT | 104 TRAINING DATA SET ACQUISITION UNIT | 106 UPDATE UNIT |
|---|---|---|
| 102 INPUT CONTROL UNIT | 105 MODEL EXECUTION UNIT | 107 END DETERMINATION UNIT |
| 103 OUTPUT CONTROL UNIT | | 108 STORAGE CONTROL UNIT |

FIG. 4

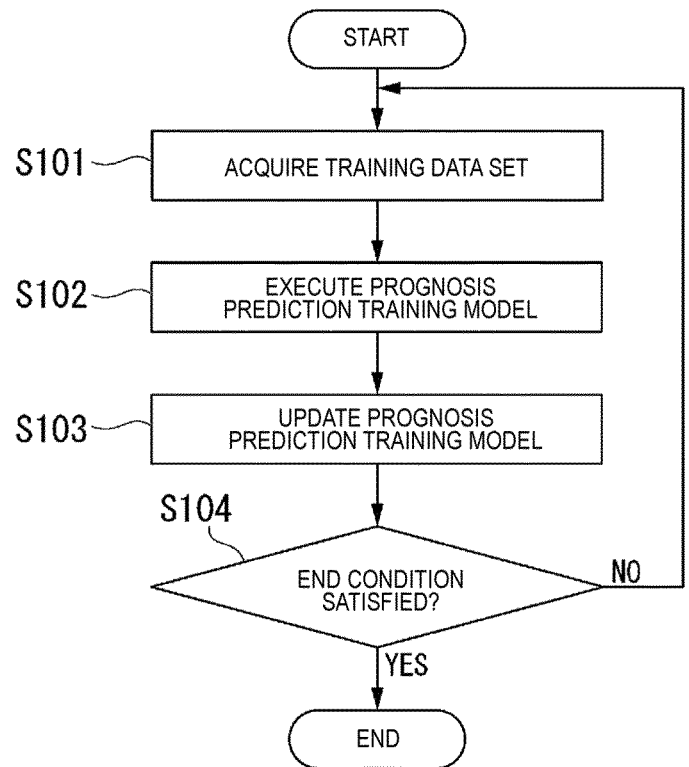

START

S101 — ACQUIRE TRAINING DATA SET

S102 — EXECUTE PROGNOSIS PREDICTION TRAINING MODEL

S103 — UPDATE PROGNOSIS PREDICTION TRAINING MODEL

S104 — END CONDITION SATISFIED?          NO

YES

END

FIG. 5

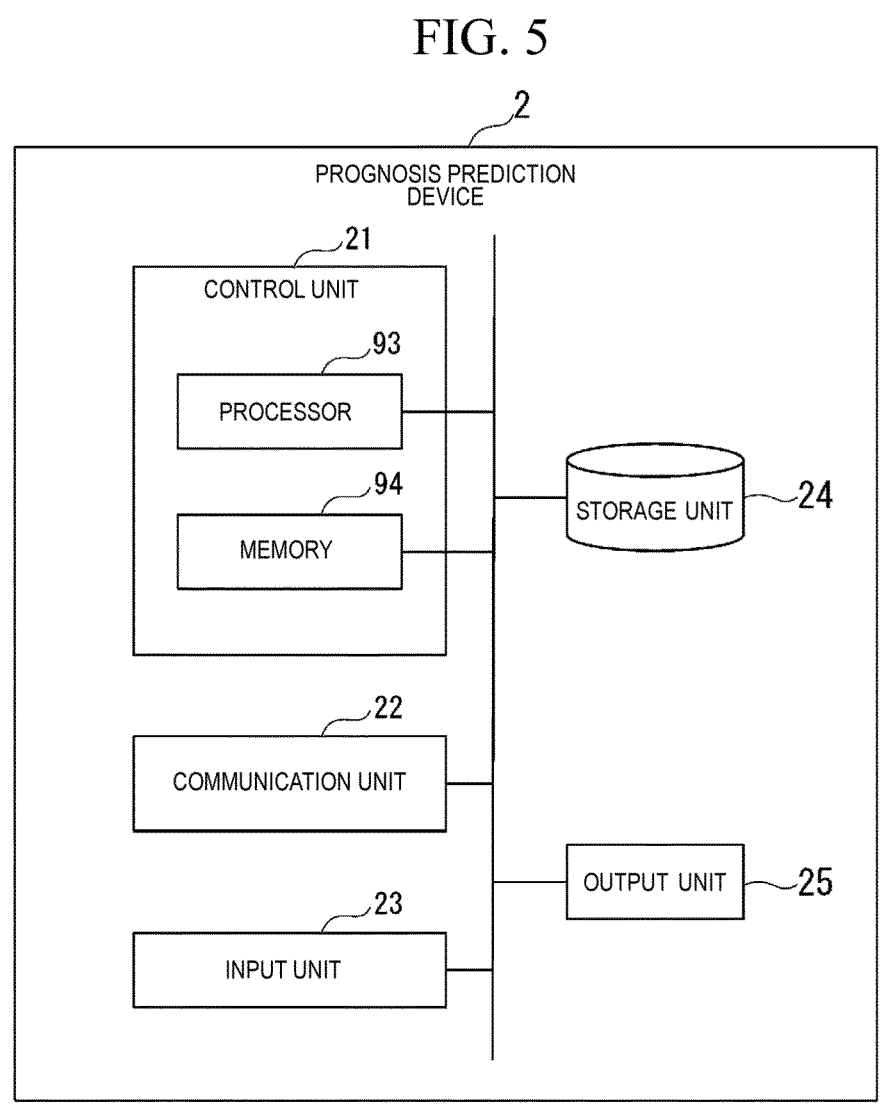

PROGNOSIS PREDICTION DEVICE — 2

CONTROL UNIT — 21

PROCESSOR — 93

MEMORY — 94

STORAGE UNIT — 24

COMMUNICATION UNIT — 22

OUTPUT UNIT — 25

INPUT UNIT — 23

FIG. 12

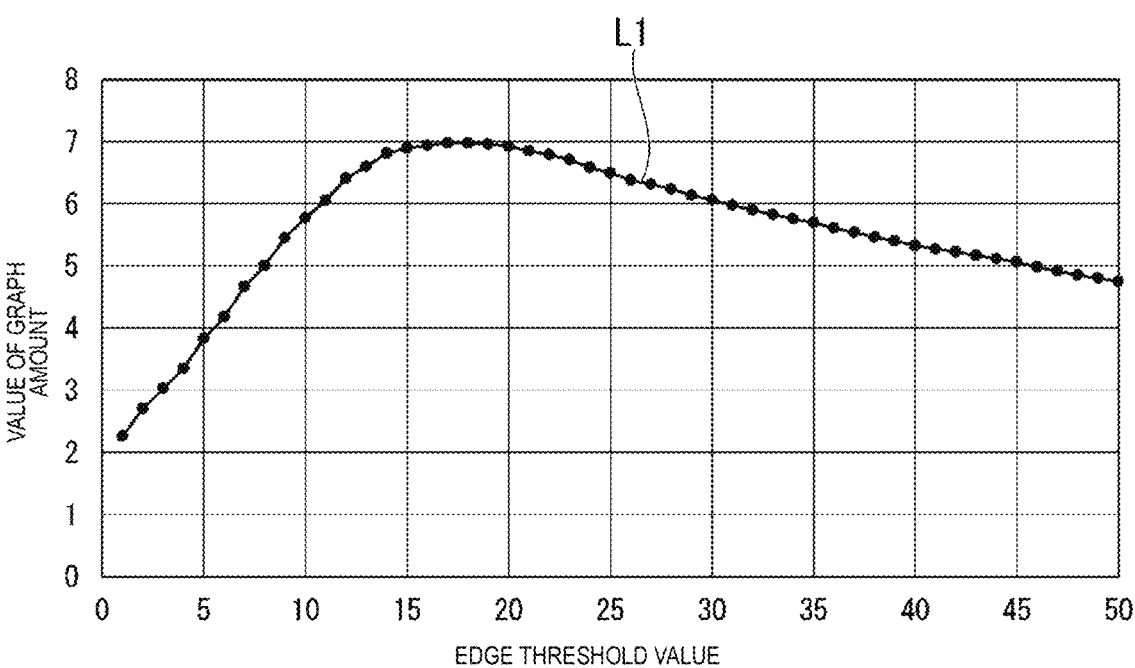

FIG. 13

|  |  | NUMBER OF PATIENTS | SURVIVAL PERIOD (MEDIAN VALUE (RANGE)) |
|---|---|---|---|
| ALL DATA |  | 304 PERSONS | 598 DAYS (1 DAY TO 3364 DAYS) |
| HISTOLOGY | ADENOCARCINOMA | 135 PERSONS | 562 DAYS (1 DAY TO 3364 DAYS) |
|  | SQUAMOUS CELL CARCINOMA | 149 PERSONS | 775 DAYS (8 DAYS TO 3253 DAYS) |
|  | LARGE CELL CARCINOMA | 7 PERSONS | 540 DAYS (279 DAYS TO 2875 DAYS) |
|  | NOS | 13 PERSONS | 967 DAYS (77 DAYS TO 2562 DAYS) |
| DISEASE STAGE | STAGE I | 83 PERSONS | 895 DAYS (10 DAYS TO 3364 DAYS) |
|  | STAGE II | 25 PERSONS | 418 DAYS (49 DAYS TO 2875 DAYS) |
|  | STAGE III | 146 PERSONS | 677.5 DAYS (19 DAYS TO 3302 DAYS) |
|  | STAGE IV | 41 PERSONS | 208 DAYS (9 DAYS TO 2824 DAYS) |

FIG. 20

| | SELECTED FEATURE | COEFFICIENT |
|---|---|---|
| FEATURE OF GRAPH THEORY | • VERTEX_NUMBER OF VERTICES | $5.259 \times 10^{-6}$ |
| | • EDGE_NUMBER OF EDGES HAVING SAME VALUE AS THRESHOLD VALUE_THRESHOLD VALUE 10 | $9.591 \times 10^{-2}$ |
| | • HISTOGRAM_NUMBER OF EDGES HAVING SAME VALUE AS THRESHOLD VALUE_APPROXIMATE CURVE y-INTERCEPT | $3.532$ |
| FEATURE IN RELATED ART | Maximum2DDiameterRow/shape | $9.924 \times 10^{-3}$ |
| | ZoneVariance/glszm | $1.917 \times 10^{-7}$ |
| | Complexity/ngtdm | $7.173 \times 10^{-5}$ |

FIG. 21

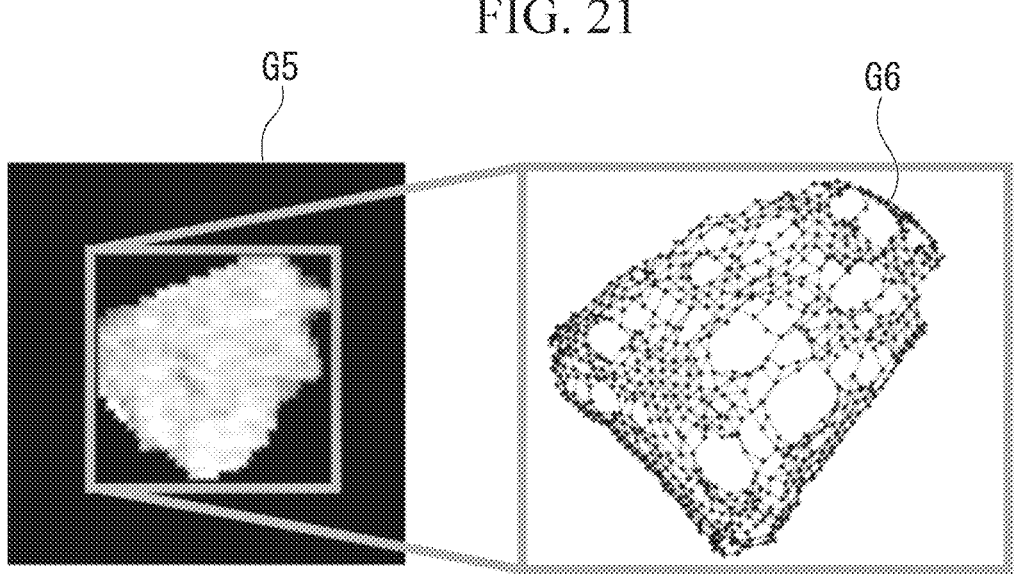

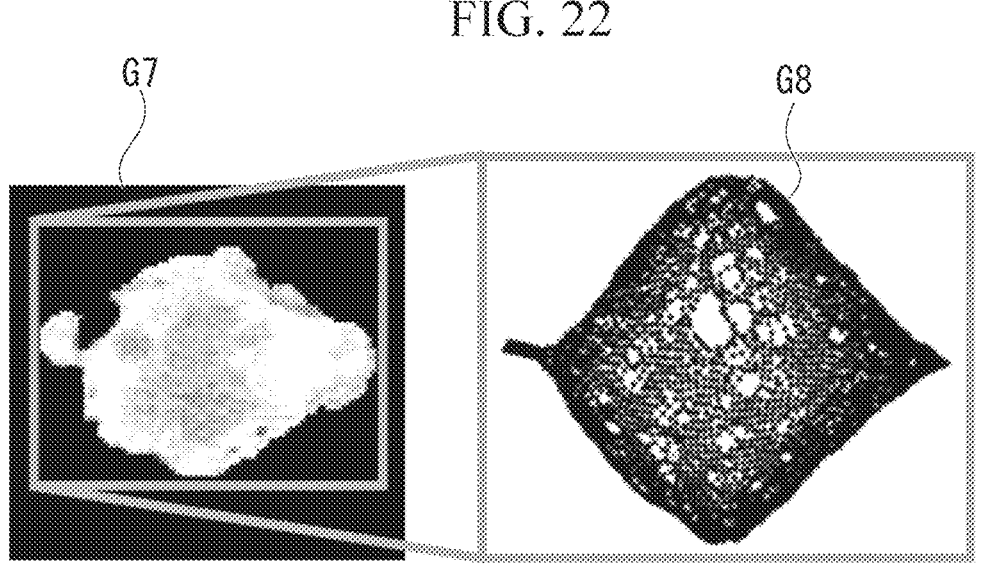

G7    G8

PROGNOSIS PREDICTION DEVICE, PROGNOSIS PREDICTION METHOD, AND PROGRAM

CROSS-REFERENCE TO RELATED APPLICATIONS

This application is national phase application of International Patent Application No. PCT/JP2022/014827, filed Mar. 28, 2022, which, in turn, is based upon and claims the right of priority to Japanese Patent Application No. 2021-060268, filed Mar. 31, 2021, the disclosures of both of which are hereby incorporated by reference herein in their entirety by reference for all purposes.

TECHNICAL FIELD

The present invention relates to a prognosis prediction device, a prognosis prediction method, and a program.

The present application claims priority based on Japanese Patent Application No. 2021-60268 filed on Mar. 31, 2021, and contents thereof are incorporated by reference.

BACKGROUND ART

In recent years, a technique called radiomics has been studied. The radiomics is a techniques for handling, in a large-scale and comprehensive manner, a relationship between a radiomics feature, which is several thousand types of phenotype information extracted from a large number of medical images, and as clinical information such pathological information, prognosis, and side effects. As one of applications of the radiomics, studies have been made on an application of the radiomics to prognosis prediction for a patient having tumor disease.

More specifically, a technique of performing prognosis prediction for a patient having tumor disease using information on a phenotype of a tumor has been studied. In such studies, it has been proposed to use, for example, a sphericity of the tumor, a square of an entire intratumor CT value, or a variation in the intratumor CT value as information on the phenotype of the tumor.

CITATION LIST

Patent Literature

PTL 1: WO2020/067481
PTL 2: JP2008-522273A

Non Patent Literature

NPL 1: Ahmed Hosny et. al., "Deep learning for lung cancer prognostication: A retrospective multi-cohort radiomics study", PLOS Medicine, 15 (11): e1002711, November 30, (2018)

SUMMARY OF INVENTION

Technical Problem

However, information on the phenotype of the tumor, such as the sphericity of the tumor, the square of the entire intratumor CT value, and the variation in the intratumor CT value, which has been proposed so far, may not be accurate, and accuracy of the information varies widely between facilities and between patients. There is a problem that it is difficult to acquire local information in a tumor based on the information on the phenotype of the tumor. Therefore, the prognosis prediction for a patient having tumor disease using information on the phenotype of the tumor may not be accurate.

In view of the above circumstances, an object of the invention is to provide a technique for improving accuracy of prognosis prediction for a patient having tumor disease.

Solution to Problem

An aspect of the invention is a prognosis prediction device including a prognosis prediction unit configured to predict, using prognosis prediction information that indicates a relationship between graph tumor information that is information on an image of a tumor represented using an amount defined by a graph theory and a prognosis of a person or an animal having the tumor, a prognosis of an estimation target based on graph tumor information indicating an image of a tumor of the estimation target.

An aspect of the invention is a prognosis prediction method having a prognosis prediction step of predicting, using prognosis prediction information that indicates a relationship between graph tumor information that is information on an image of a tumor represented using an amount defined by a graph theory and a prognosis of a person or an animal having the tumor, a prognosis of an estimation target based on graph tumor information indicating an image of a tumor of the estimation target.

One aspect of the invention is a program for causing the above prognosis prediction device to function as a computer.

Advantageous Effects of Invention

According to the invention, it is possible to improve accuracy of prognosis prediction for a patient having tumor disease.

BRIEF DESCRIPTION OF DRAWINGS

FIG. 3 is a diagram showing an example of a functional configuration of a control unit 11 according to the embodiment.

FIG. 4 is a flowchart showing an example of a flow of processing executed by the prognosis prediction information acquisition device 1 according to the embodiment.

FIG. 5 is a diagram showing an example of a hardware configuration of a prognosis prediction device 2 according to the embodiment.

FIG. 12 is a third diagram showing an example of the graph amount according to the embodiment.

FIG. 13 is a first diagram showing an experiment according to the embodiment.

FIG. 20 is an eighth diagram showing an experiment according to the embodiment.

FIG. 21 is a ninth diagram showing an experiment according to the embodiment.

FIG. 22 is a tenth diagram showing an experiment according to the embodiment.

DESCRIPTION OF EMBODIMENTS

Embodiment

Figure 1:
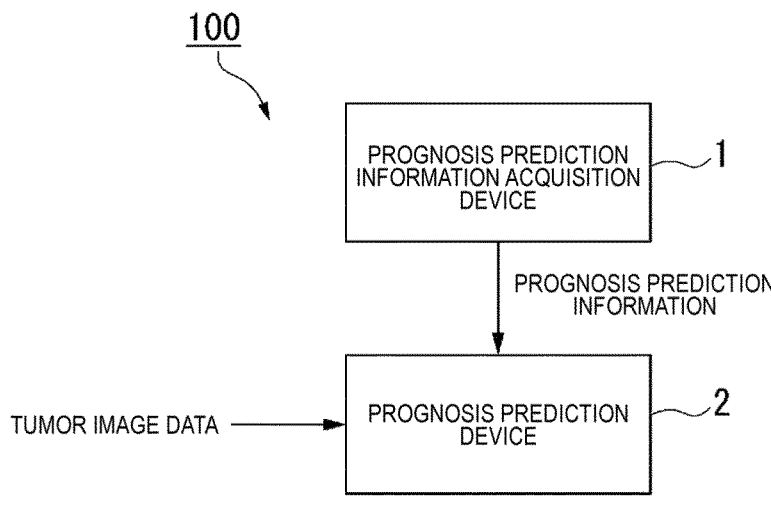
FIG. 1 is a diagram showing an outline of a prognosis prediction system 100 according to an embodiment.

FIG. 1 is a diagram showing an outline of a prognosis prediction system 100 according to an embodiment. The prognosis prediction system 100 includes a prognosis prediction information acquisition device 1 and a prognosis prediction device 2.

The prognosis prediction information acquisition device 1 acquires information indicating a relationship between information on an image of a tumor (hereinafter referred to as "tumor image") shown in an image and represented using a graph amount (hereinafter, referred to as "graph tumor information") and prognosis of a patient having tumor disease (hereinafter, referred to as "prognosis prediction information"). The patient having the tumor disease is an example of a person or an animal having a tumor. The graph amount is an amount defined by a graph theory. The graph amount may be any amount defined by the graph theory.

An image showing a tumor image (hereinafter referred to as "tumor image") may be any image as long as the image is an image obtained by a technique capable of showing a tumor. The tumor image is, for example, a computed tomography (CT) image. The tumor image may be, for example, a magnetic resonance imaging (MRI) image or an ultrasonic image.

The graph amount is information indicating a topology of a graph in the graph theory, for example. Specifically, the information indicating the topology in the graph theory is information indicating at least a positional relationship of each vertex in the graph. The graph amount is, for example, a weight of a vertex defined by the graph theory. Therefore, the graph amount may be an amount indicating a positional relationship between vertices for which weights are defined and a weight of each vertex. The graph amount may be, for example, a weight of an edge defined by the graph theory. The graph amount may be, for example, a degree of a vertex defined by the graph theory.

The graph amount may be, for example, an adjacency matrix defined by the graph theory. The graph amount may be, for example, a degree matrix defined by the graph theory. The graph amount may be, for example, a connection matrix defined by the graph theory.

The graph amount may be, for example, eccentricity defined by the graph theory. The graph amount may be, for example, a radius of a graph defined by the graph theory. The graph amount may be, for example, a diameter of a graph defined by the graph theory.

The graph amount may be, for example, an amount related to a path of the graph. The amount related to the path of the graph may be, for example, an amount related to a minimum spanning tree of the graph (see Reference Document 1). For example, when the graph is an Eulerian cycle, the amount related to the path of the graph may be an amount related to the Eulerian cycle. For example, when the graph is a Hamiltonian cycle, the amount related to the path of the graph may be an amount related to the Hamiltonian cycle.

Reference Document 1: "Combinatorial Optimization: Theory and Algorithms Second Edition" written by Bernhard Korte and Jens Vygen (translated by Takao Asano, Yasuhito Asano, Takao Ono, Tomio Hirata), Maruzen Publishing, 2012, pp. 160-163

The graph tumor information may be expressed using the graph amount. Therefore, the graph tumor information does not necessarily need to be expressed only by the graph amount. The graph tumor information may be expressed by, for example, information indicating a relationship between a plurality of graph amounts.

The information indicating the relationship between the plurality of graph amounts may be, for example, information indicating whether a graph expressing information on a tumor (hereinafter, referred to as a "tumor expression graph") is an undirected graph. The information indicating the relationship between the plurality of graph amounts may be, for example, information indicating whether the tumor expression graph is a directed graph. The information indicating the relationship between the plurality of graph amounts may be, for example, information indicating whether the tumor expression graph is a product graph. The information indicating the relationship between the plurality of graph amounts may be, for example, information indicating whether the tumor expression graph is a regular graph.

The information indicating the relationship between the plurality of graph amounts is, for example, information indicating whether the tumor expression graph is an Eulerian cycle. The information indicating the relationship between the plurality of graph amounts may be, for example, information indicating whether the tumor expression graph is a Hamiltonian cycle.

The information indicating the relationship between the plurality of graph amounts may be, for example, information indicating whether an adjacency matrix indicating information on a tumor has a property of a predetermined matrix such as whether the adjacency matrix is a Hermitian matrix. The information indicating the relationship between the plurality of graph amounts may be, for example, information indicating whether a degree matrix indicating information on a tumor has a property of a predetermined matrix such as whether the degree matrix is a Hermitian matrix. The information indicating the relationship between the plurality of graph amounts may be, for example, information indicating whether a connection matrix indicating information on a tumor has a property of a predetermined matrix such as whether the connection matrix is a Hermitian matrix.

The information indicating the relationship between the plurality of graph amounts may be, for example, information indicating a difference between a tumor expression graph and a predetermined reference graph. The information indicating the difference between the tumor expression graph and the predetermined reference graph is, for example, information indicating whether the tumor expression graph and the predetermined reference graph are of the same type.

The prognosis prediction information is, for example, a learned training model acquired by a machine learning method. Hereinafter, for simplification of description, the prognosis prediction system 100 will be described by taking a case where the prognosis prediction information is a learned training model acquired by a machine learning method as an example.

The prognosis prediction information acquisition device 1 updates a training model for predicting prognosis of a person or an animal having a tumor indicated by the graph tumor information based on the graph tumor information (hereinafter, referred to as a "prognosis prediction training model") by a machine learning method.

The training model is a mathematical model including one or more pieces of processing in which conditions and orders for execution (hereinafter, referred to as "execution rule") are predetermined. Hereinafter, for simplification of description, an update of the training model by a machine learning method is referred to as learning. The update of the training model means suitably adjusting a value of a parameter in the training model. Execution of the training model means that processing in the training model is executed according to the execution rule.

The training model is represented by, for example, a neural network. The neural network is a circuit, such as an electronic circuit, an electric circuit, an optical circuit, or an integrated circuit, which represents a training model. The update of the training model is also an update of the neural network representing the training model by learning. The update of the neural network by learning means that a value of a parameter of the neural network is updated. The parameter of the neural network is a parameter of a circuit constituting the neural network, and is also a parameter of a training model represented by the circuit constituting the neural network.

The neural network that represents the prognosis prediction training model may be any neural network that can represent the prognosis prediction training model. The neural network that represents the prognosis prediction training model is, for example, a deep neural network.

More specifically, the prognosis prediction information acquisition device 1 updates the prognosis prediction training model by a machine learning method using graph tumor information as an explanatory variable and using prognosis information as a ground truth label (that is, objective variable) of the pair of pieces of the graph tumor information and the prognostic information. The prognosis information is information indicating prognosis. Hereinafter, a pair of pieces of graph tumor information and prognosis information is referred to as a training data set.

The prognosis prediction information acquisition device 1 updates the prognosis prediction training model until a predetermined end condition (hereinafter, referred to as "learning end condition") is satisfied. The learning end condition is, for example, a condition that learning using a predetermined number of training data sets is performed. The learned prognosis prediction training model is an example of the prognosis prediction information. The learned prognosis prediction training model is a prognosis prediction training model at a timing when the learning end condition is satisfied.

The prognosis prediction device 2 receives image data of a tumor image (hereinafter referred to as "tumor image data"). The prognosis prediction device 2 predicts a prognosis of a prediction target having a subject tumor using the prognosis prediction information. The subject tumor is a tumor in the tumor image indicated by the tumor image data. The prediction target is a person or an animal. The prediction target is, for example, a patient. The prognosis prediction information used by the prognosis prediction device 2 is, for example, prognosis prediction information obtained the by prognosis prediction information acquisition device 1. Therefore, the prognosis prediction information used by the prognosis prediction device 2 is, for example, a learned prognosis prediction training model.

A pair of pieces of tumor image data and prognosis information (hereinafter referred to as "unprocessed training data set") is input to the prognosis prediction information acquisition device 1. The prognosis prediction information acquisition device 1 generates one or more training data sets based on the unprocessed training data set according to a predetermined rule. Hereinafter, processing of generating one or more training data sets based on the unprocessed training data set is referred to as training data set generation processing. The training data set generation processing is processing of generating one or more training data sets based on the training data set, by generating one or more pieces of graph tumor information based on tumor image data in the unprocessed training data set.

The graph tumor information generated based on the tumor image data is information indicating an image of a tumor in a tumor image indicated by the tumor image data, and is information indicating a value of a predefined graph amount. Processing of generating one or more pieces of graph tumor information based on the tumor image data is, for example, processing of calculating a value of a predefined graph amount based on the tumor image data. Hereinafter, the processing of generating one or more pieces of graph tumor information based on the tumor image data is referred to as graph tumor information acquisition processing.

Figure 2:
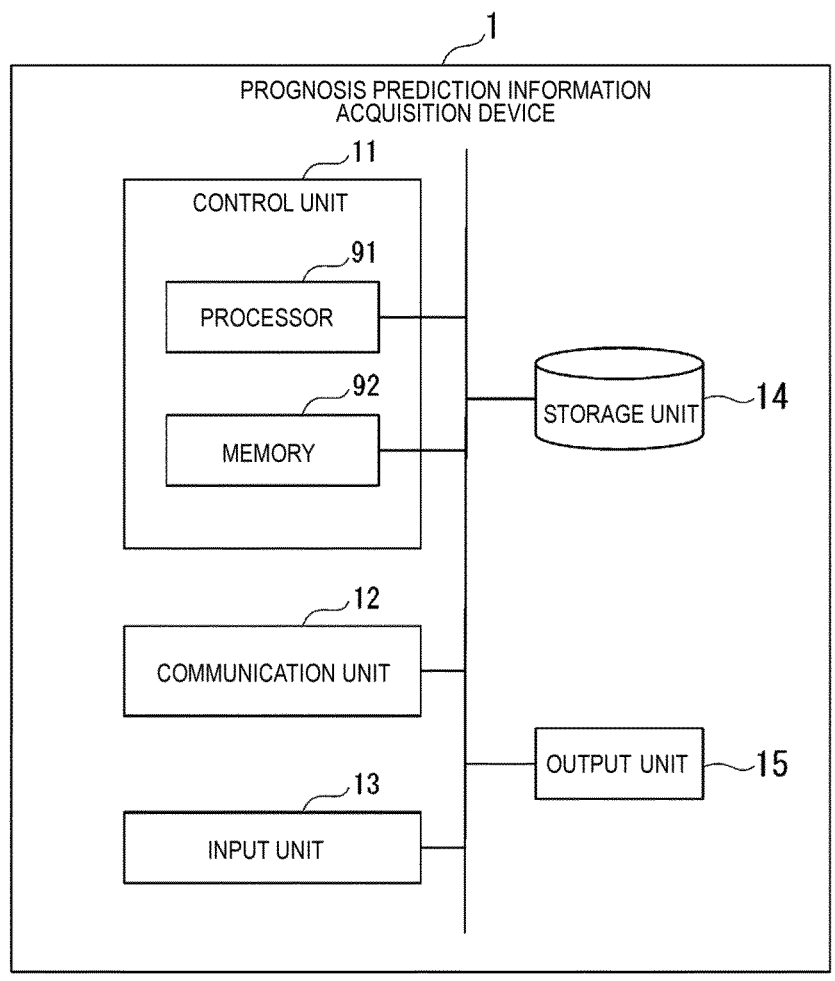
FIG. 2 is a diagram showing an example of a hardware configuration of a prognosis prediction information acquisition device 1 according to the embodiment.

FIG. 2 is a diagram showing an example of a hardware configuration of the prognosis prediction information acquisition device 1 according to the embodiment. The prognosis prediction information acquisition device 1 includes a control unit 11 including a processor 91 such as a central processing unit (CPU) and a memory 92 connected by a bus, and executes a program. The prognosis prediction information acquisition device 1 functions as a device including the control unit 11, a communication unit 12, an input unit 13, a storage unit 14, and an output unit 15 by executing a program.

More specifically, the processor 91 reads a program stored in the storage unit 14 and stores the read program in the memory 92. By the processor 91 executing the program stored in the memory 92, the prognosis prediction information acquisition device 1 functions as a device including the control unit 11, the communication unit 12, the input unit 13, the storage unit 14, and the output unit 15.

The control unit 11 controls operations of various functional units in the prognosis prediction information acquisition device 1. The control unit 11 executes, for example, training data set generation processing. The control unit 11 executes, for example, a prognosis prediction training model.

The control unit 11 controls, for example, an operation of the output unit 15. For example, the control unit 11 records various types of information generated by execution of the prognosis prediction training model in the storage unit 14. For example, the control unit 11 records information input to the communication unit 12 or the input unit 13 in the storage unit 14.

The communication unit 12 includes a communication interface for connecting the prognosis prediction information acquisition device 1 to an external device. The communication unit 12 communicates with the external device in a wired or wireless manner. The external device is, for example, a transmission source device for an unprocessed training data set. The communication unit 12 communicates with the transmission source device for the unprocessed training data set to receive the unprocessed training data set transmitted by the transmission source device for the unprocessed training data set. The external device is, for example, the prognosis prediction device 2. The communication unit 12 transmits, for example, prognosis prediction information to the prognosis prediction device 2 through communication with the prognosis prediction device 2. The prognosis prediction information transmitted from the communication unit 12 to the prognosis prediction device 2 is, for example, a learned prognosis prediction training model.

The input unit 13 includes an input device such as a mouse, a keyboard, or a touch panel. The input unit 13 may be configured as an interface that connects the input device to the prognosis prediction information acquisition device 1. The input unit 13 receives input of various types of information to the prognosis prediction information acquisition device 1. For example, an instruction to start learning is input to the input unit 13. The unprocessed training data set may be input to the input unit 13.

The storage unit 14 is implemented using a computer readable storage medium device such as a magnetic hard disk device or a semiconductor storage device. The storage unit 14 stores various types of information related to the prognosis prediction information acquisition device 1. The storage unit 14 stores, for example, information input via the input unit 13 or the communication unit 12. The storage unit 14 stores, for example, various types of information generated by execution of the prognosis prediction training model.

The unprocessed training data set does not need to be input only to the communication unit 12 or only to the input unit 13. The unprocessed training data set may be input via either the communication unit 12 or the input unit 13. The unprocessed training data set may be stored in the storage unit 14 in advance.

The output unit 15 outputs various types of information. The output unit 15 includes a display device such as a cathode ray tube (CRT) display, a liquid crystal display, or an organic electro-luminescence (EL) display. The output unit 15 may be configured as an interface that connects the display device to the prognosis prediction information acquisition device 1. The output unit 15 outputs, for example, information input to the input unit 13. The output unit 15 may display, for example, an execution result of the prognosis prediction training model. For example, the output unit 15 may output the graph tumor information in a training data set generated by executing the training data set generation processing.

FIG. 3 is a diagram showing an example of a functional configuration of the control unit 11 according to the embodiment. The control unit 11 includes a communication control unit 101, an input control unit 102, an output control unit 103, a training data set acquisition unit 104, a model execution unit 105, an update unit 106, an end determination unit 107, and a storage control unit 108.

The communication control unit 101 controls an operation of the communication unit 12. Under the control of the communication control unit 101, the communication unit 12 transmits the learned prognosis prediction training model (that is, prognosis prediction information) to the prognosis prediction device 2. The input control unit 102 controls an operation of the input unit 13. The output control unit 103 controls an operation of the output unit 15.

The training data set acquisition unit 104 executes training data set generation processing on the unprocessed training data set. The training data set acquisition unit 104 generates one or more training data sets by executing the training data set generation processing. Thus, the training data set acquisition unit 104 acquires the training data set by generating the training data set by executing the training data set generation processing.

The unprocessed training data set to be subjected to the training data set generation processing by the training data set acquisition unit 104 is, for example, an unprocessed training data set input to the communication unit 12 or the input unit 13. The unprocessed training data set to be subjected to the training data set generation processing by the training data set acquisition unit 104 may be, for example, the unprocessed training data set stored in the storage unit 14 when the unprocessed training data set has been recorded in the storage unit 14 in advance.

The model execution unit 105 executes a prognosis prediction training model on the graph tumor information in the training data set acquired by the training data set acquisition unit 104. The model execution unit 105 predicts a prognosis of a person or an animal having a tumor indicated by the graph tumor information acquired by the training data set acquisition unit 104 by executing the prognosis prediction training model.

The update unit 106 updates the prognosis prediction training model based on a prediction loss. The prediction loss is a difference between a prediction result of the model execution unit 105 and a ground truth label (that is, prognosis information) in the training data set acquired by the training data set acquisition unit 104.

Both the prediction result of the model execution unit 105 and the prognosis information are represented by, for example, a first-order tensor (that is, vector). Both the prediction result of the model execution unit 105 and the prognosis information may be represented by, for example, a second-order tensor (that is, matrix). Both the prediction result of the model execution unit 105 and the prognosis information may be represented by, for example, a third or higher order tensor. The prediction loss is represented by, for example, an inverse of an inner product of a tensor representing the prediction result of the model execution unit 105 and a tensor representing the prognosis information. The larger a value of the inner product, the smaller the difference between the tensor representing the prediction result of the model execution unit 105 and the tensor representing the prognosis information, and the smaller the prediction loss.

The end determination unit 107 determines whether the learning end condition is satisfied. The storage control unit 108 records various types of information in the storage unit 14.

FIG. 4 is a flowchart showing an example of a flow of processing to be executed by the prognosis prediction information acquisition device 1 according to the embodiment. Unprocessed training data set is input to the communication unit 12 or the input unit 13, and the training data set acquisition unit 104 acquires training data set by executing the training data set generation processing for the input unprocessed training data set (step S101).

Next, the model execution unit 105 executes the prognosis prediction training model on graph tumor information in the training data set acquired in step S101 (step S102). By executing the prognosis prediction training model, the model execution unit 105 predicts a prognosis of a person or an animal having a tumor indicated by the graph tumor information acquired in step S101.

Next, the update unit 106 updates the prognosis prediction training model so as to reduce a difference (that is, prediction loss) between a prediction result obtained in step S102 and a ground truth label in the training data set obtained in step S101 (step S103) based on the difference.

Next, the end determination unit 107 determines whether the learning end condition is satisfied (step S104). If the learning end condition is satisfied (step S104: YES), the processing ends. On the other hand, if the learning end condition is not satisfied (step S104: NO), the processing returns to step S101.

FIG. 5 is a diagram showing an example of a hardware configuration of the prognosis prediction device 2 according to the embodiment. The prognosis prediction device 2 includes a control unit 21 including a processor 93 such as a CPU and a memory 94 connected by a bus, and executes a program. The prognosis prediction device 2 functions as a device including the control unit 21, a communication unit 22, an input unit 23, a storage unit 24, and an output unit 25 by executing a program.

More specifically, in the prognosis prediction device 2, the processor 93 reads a program stored in the storage unit 24 and stores the read program in the memory 94. By the processor 93 executing the program stored in the memory 94, the prognosis prediction device 2 functions as a device including the control unit 21, the communication unit 22, the input unit 23, the storage unit 24, and the output unit 25.

The control unit 21 controls operations of various functional units in the prognosis prediction device 2. The control unit 21 acquires, for example, tumor image data showing an image of a tumor as the prediction target. The control unit 21 predicts a prognosis of the prediction target using the prognosis prediction information based on the acquired tumor image data. Hereinafter, processing of predicting the prognosis of the prediction target using the prognosis prediction information based on the tumor image data is referred to as prognosis prediction processing.

The prognosis prediction processing includes preprocessing and main processing. The preprocessing is executed before execution of the main processing. The preprocessing is processing of generating one or more pieces of graph tumor information based on tumor image data. The preprocessing is, for example, processing of calculating, based on the tumor image data, a value of a graph amount that is predetermined and defined in training data generation processing. The preprocessing may be any processing as long as the processing generates one or more pieces of graph tumor information based on the tumor image data, and may be, for example, processing similar to the graph tumor information acquisition processing executed in the training data set generation processing.

The main processing is processing of predicting a prognosis of the prediction target using prognosis prediction information based on the graph tumor information obtained in the preprocessing. The main processing is, for example, processing of executing a learned prognosis prediction training model on graph tumor information obtained in the preprocessing.

The control unit 21 records, for example, an execution result of the prognosis prediction processing in the storage unit 24. The control unit 21 controls, for example, an operation of the communication unit 22.

The communication unit 22 includes a communication interface for connecting the prognosis prediction device 2 to an external device. The communication unit 22 communicates with the external device in a wired or wireless manner. The external device to which the communication unit 22 communicates is, for example, the prognosis prediction information acquisition device 1. The communication unit 22 receives the prognosis prediction information transmitted by the prognosis prediction information acquisition device 1 through, for example, communication with the prognosis prediction n information acquisition device 1.

The external device may be, for example, a transmission source device for tumor image data. In such a case, the communication unit 22 receives the tumor image data through communication with the transmission source device for the tumor image data. The external device is, for example, a tumor image capturing device. The tumor image capturing device is, for example, a CT device. The tumor image capturing device may be, for example, an MRI device.

The input unit 23 includes an input device such as a mouse, a keyboard, or a touch panel. The input unit 23 may be configured as an interface that connects the input device to the prognosis prediction device 2. The input unit 23 receives input of various types of information to the prognosis prediction device 2. For example, the tumor image data may be input to the input unit 23.

The storage unit 24 is implemented using a computer readable storage medium device such as a magnetic hard disk device or a semiconductor storage device. The storage unit 24 stores various types of information related to the prognosis prediction device 2. The storage unit 24 stores in advance, for example, a program for controlling operations of the functional units in the prognosis prediction device 2. The storage unit 24 stores, for example, prognosis prediction information. The prognosis prediction information stored in the storage unit 24 is prognosis prediction information obtained by the prognosis prediction information acquisition device 1. The storage unit 24 stores, for example, a prediction result obtained by the prognosis prediction device 2.

The tumor image data does not need to be input only to the communication unit 22 or only to the input unit 23. The tumor image data may be input via either the communication unit 22 or the input unit 23.

The output unit 25 outputs various types of information. The output unit 25 includes a display device such as a CRT display, a liquid crystal display, or an organic EL display. The output unit 25 may be configured as an interface that connects the display device to the prognosis prediction device 2. The output unit 25 outputs, for example, information input to the input unit 23. The output unit 25 may display a tumor image indicated by the tumor image data input to the communication unit 22 or the input unit 23, for example. The output unit 25 may display, for example, an execution result of the prognosis prediction processing.

Figure 6:
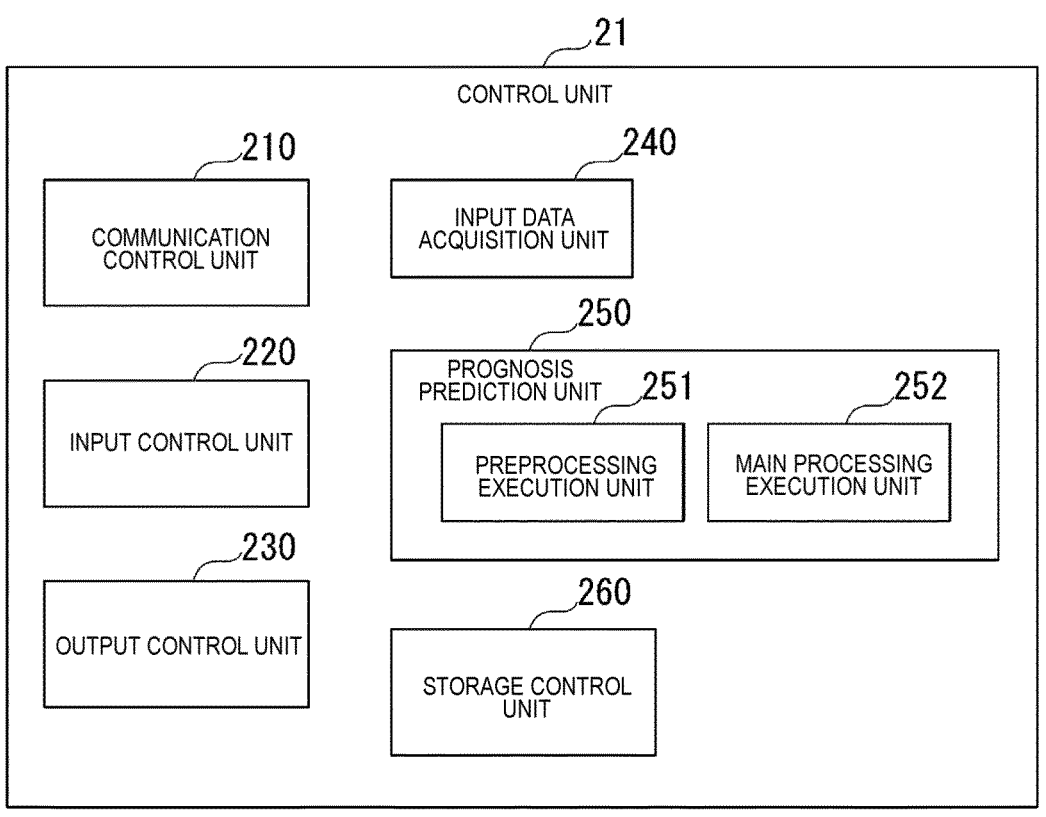
FIG. 6 is a diagram showing an example of a functional configuration of a control unit 21 according to the embodiment.

FIG. 6 is a diagram showing an example of a functional configuration of the control unit 21 according to the embodiment. The control unit 21 includes a communication control unit 210, an input control unit 220, an output control unit 230, an input data acquisition unit 240, a prognosis prediction unit 250, and a storage control unit 260.

The communication control unit 210 controls an operation of the communication unit 22. The input control unit 220 controls an operation of the input unit 23. The output control unit 230 controls an operation of the output unit 25.

The input data acquisition unit 240 acquires data input to the communication unit 22 or the input unit 23. The input data acquisition unit 240 acquires tumor image data input to the communication unit 22 or the input unit 23, for example. For example, when the tumor image data is input to the communication unit 22 or the input unit 23 in advance and the tumor image data is recorded in the storage unit 24 in advance, the input data acquisition unit 240 may read the tumor image data from the storage unit 24.

The prognosis prediction unit 250 executes prognosis prediction processing on the tumor image data acquired by the input data acquisition unit 240. By executing the prognosis prediction processing, the prognosis prediction unit 250 predicts a prognosis of a person or an animal (that is, prediction target) having a subject tumor.

The prognosis prediction unit 250 includes a preprocessing execution unit 251 and a main processing execution unit 252. The preprocessing execution unit 251 executes the preprocessing. The main processing execution unit 252 executes the main processing. The prognosis prediction processing executed by the prognosis prediction unit 250 is, for example, processing in which the preprocessing execution unit 251 executes preprocessing on the tumor image data acquired by the input data acquisition unit 240, and the main processing execution unit 252 executes main processing on the graph tumor information obtained by the preprocessing execution unit 251. A tumor in an image indicated by the tumor image data acquired by the input data acquisition unit 240 is a tumor of an estimation target. The graph tumor information indicating the image of the tumor of the estimation target is obtained by executing preprocessing on the tumor image data acquired by the input data acquisition unit 240. Therefore, the prognosis prediction unit 250 predicts a prognosis of the estimation target based on the graph tumor information indicating the image of the tumor of the estimation target.

The storage control unit 206 records various types of information in the storage unit 24.

Figure 7:
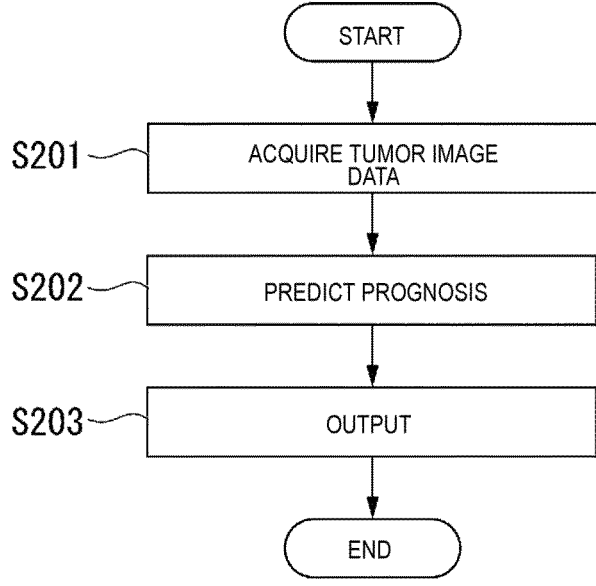
FIG. 7 is a flowchart showing an example of a flow of processing executed by the prognosis prediction device 2 according to the embodiment.

FIG. 7 is a flowchart showing an example of a flow of processing to be executed by the prognosis prediction device 2 according to the embodiment. The input data acquisition unit 240 acquires tumor image data indicating an image of a tumor of an estimation target (step S201). The estimation target is a person or an animal who is an estimation target of prognosis prediction by the prognosis prediction device 2. Next, the prognosis prediction unit 250 predicts a prognosis of the estimation target by executing the prognosis prediction processing (step S202). The output control unit 230 controls an operation of the output unit 25 to cause the output unit 25 to display a prediction result obtained in step S202 (step S203).

<Relationship Between Tumor Image and Graph Tumor Information>

Figure 8:
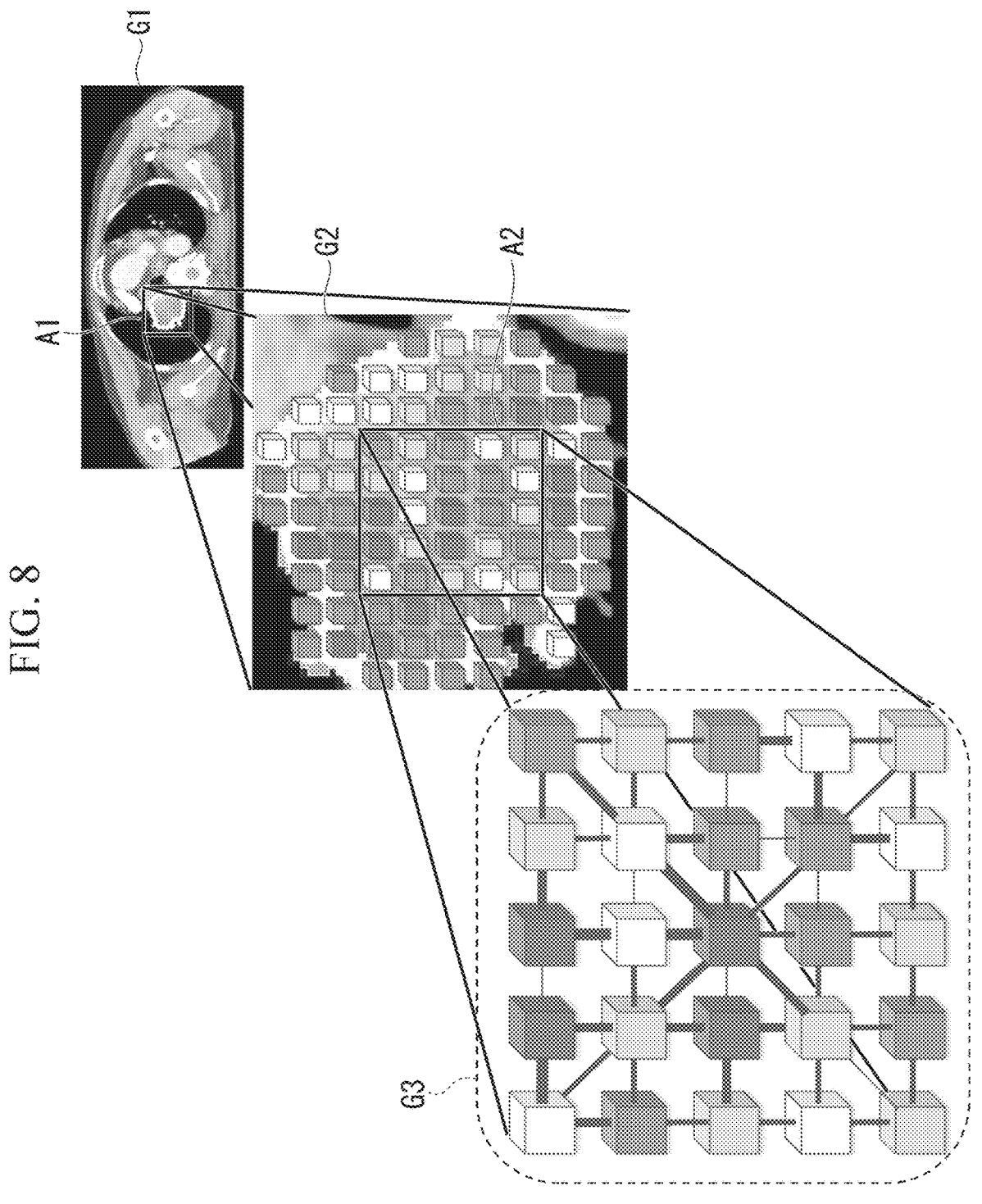
FIG. 8 is a first diagram showing an example of a relationship between a tumor image and graph tumor information according to the embodiment.

FIG. 8 is a first diagram showing an example of a relationship between a tumor image and graph tumor information according to the embodiment. FIG. 8 shows three images of an image G1, an image G2, and an image G3, and a relationship therebetween. The image G1 in FIG. 8 is an example of an image (that is, tumor image) indicated by tumor image data. The image G1 shows a cross-sectional view of a chest of an estimation target. The image G1 also shows a cross-sectional view of a tumor of the estimation target. An image of a region A1 in the image G1 is the cross-sectional view of the tumor of the estimation target.

The image G2 in FIG. 8 is a diagram in which an example of vertices in a graph theory representing the tumor in the region A1 is superimposed on the image of the region A1. Hereinafter, for simplicity of description, vertices in the graph theory are simply referred to as vertices. Hereinafter, for simplicity of description, an edge in the graph theory is simply referred to as an edge. Hereinafter, for simplicity of description, a graph in the graph theory is simply referred to as a graph.

In the image G2, one vertex exists for each pixel of the image of the region A1. Therefore, a positional relationship of vertices is the same as a positional relationship of pixels. A color of each vertex indicated by the image G2 represents a pixel value of each corresponding pixel in the image of the region A1. The image of the region A1 is a grayscale image. Therefore, the pixel value represented by the vertex of the image G2 is scalar. The pixel value is, for example, a CT value.

The image G3 indicates vertices existing in a region A2 in the image G2. The image G3 shows an example of edges. An edge connects a vertex and a vertex. However, an edge does not always exist between a vertex and a vertex of all vertices. Edges shown in FIG. 8 are edges connecting vertices whose absolute value of a difference in pixel values is equal to or larger than a predetermined threshold value.

In the example of FIG. 8, the vertex is defined for each pixel of the tumor image. However, the vertex is not necessarily defined for each pixel. The vertex does not need to be defined for each pixel as long as the vertex is defined for each predefined unit pixel. The unit pixel is a collection of one or more pixels adjacent to each other. The unit pixel is, for example, a 3×3 pixel.

When one vertex corresponds to one pixel as in the example of FIG. 8, the vertex represents the pixel value of the corresponding pixel. The pixel value represented by the vertex is an example of a pixel index value. The pixel index value is a predefined index value related to the pixel value of each pixel in the unit pixel. The pixel value represented by the vertex is an example of a weight of the vertex.

The pixel index value is, for example, a pixel value itself when the image is an image such as a grayscale image and a monochrome image in which a pixel value is scalar, and the unit pixel is one pixel. The pixel index value is a statistic of a distribution of pixel values of pixels in a unit pixel when the image is an image such as a grayscale image and a monochrome image in which a pixel value is scalar, and the unit pixel is a plurality of pixels. The statistic may be a representative value or a dispersion. The representative value may be, for example, an average value, a median value, a maximum value, or a minimum value. The dispersion is, for example, a standard deviation.

The pixel index value is, for example, a scalar index indicating a tensor representing a pixel value when an image is an image in which a pixel value of a color image or the like is represented by a first or higher order tensor and a unit pixel is one pixel. The scalar index indicating a tensor representing a pixel value is, for example, a magnitude of a vector when the tensor is a vector (that is, first-order tensor). The scalar index indicating a tensor representing a pixel value is, for example, a value of a determinant when the tensor is a matrix (that is, second-order tensor). The scalar index indicating a tensor representing a pixel value is, for example, a sum of squares of each element when the tensor is a third or higher order tensor. The pixel index value represented by the vertex is an example of the weight of the vertex.

Thus, the vertex is an amount defined for each unit pixel of the tumor image. Therefore, the graph tumor information using the vertex as the graph amount includes information indicating a position of a corresponding unit pixel in the tumor image for each vertex (hereinafter, referred to as "unit pixel position information"). The position of each unit pixel in the tumor image in the unit pixel position information is indicated by, for example, a position of a center of gravity of each unit pixel. The position of each unit pixel in the tumor image in the unit pixel position information may be indicated by, for example, a position of a predetermined end of each unit pixel.

In FIG. 8, only edges that satisfy the condition that an absolute value of a difference in pixel values between vertices connected by an edge is equal to or larger than the predetermined threshold value exist. That is, in the example of FIG. 8, the graph tumor information includes an edge as the graph amount, and the edge satisfies the condition that an absolute value of a difference in pixel values between vertices is equal to or larger than the predetermined threshold value. However, the edge in the graph tumor information does not necessarily have to satisfy the condition that an absolute value of a difference in pixel values between vertices connected by an edge is equal to or larger than the predetermined threshold value.

The edge in the graph tumor information may be any edge that satisfies a condition (hereinafter referred to as "edge condition") that a difference between pixel index values of two vertices connected by the edge satisfies a predetermined condition related to the difference (hereinafter, referred to as a "difference condition"). The edge in the graph tumor information is an edge of the graph. The difference condition is, for example, a condition that an absolute value of a difference between pixel index values of two vertices connected by an edge is a predetermined value or less. The difference condition may be, for example, a condition that a ratio of pixel index values of two vertices connected by an edge is within a predetermined range. The difference between pixel index values of two vertices connected by an edge is an example of a weight of the edge.

For simplicity of description, the prognosis prediction system 100 will be described by taking, as an example, a case in which the unit pixel is one pixel, the image is a grayscale image, and the difference condition is a condition in which an absolute value of a difference between pixel index values of two vertices connected by an edge is equal to or smaller than a predetermined value (hereinafter, referred to as "edge threshold value").

Figure 9:
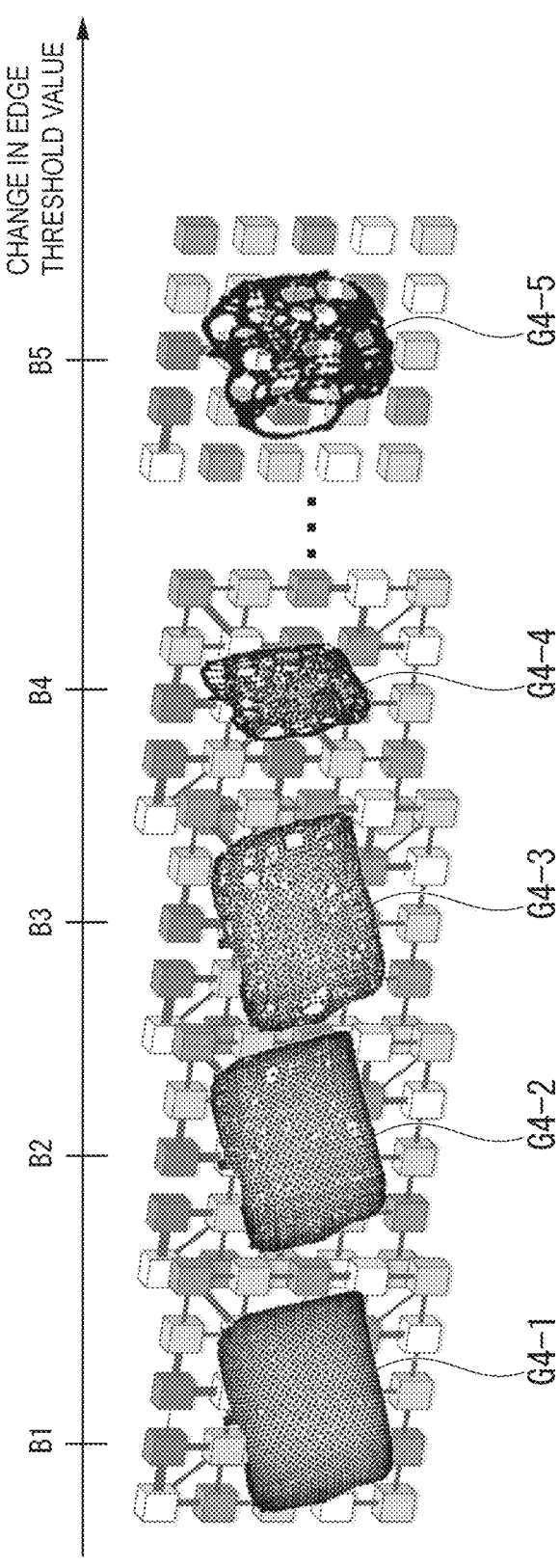
FIG. 9 is a second diagram showing an example of the relationship between a tumor image and graph tumor information according to the embodiment.

FIG. 9 is a second diagram showing an example of the relationship between a tumor image and graph tumor information according to the embodiment. More specifically, FIG. 9 is a diagram showing an example of a change in a graph when the edge threshold value is changed. The edge threshold value was 5 HU at minimum and 50 HU at maximum. As the edge threshold value, 10 values separated by 5 HU intervals from 5 HU to 50 HU were used.

FIG. 9 shows an image 4-1, an image 4-2, an image 4-3, an image 4-4, and an image 4-5. The image 4-1 to the image 4-5 are graphs showing the same tumor image. FIG. 9 shows that the graphs of the image 4-1 to the image 4-5 are different in topology. The difference in topology despite showing the same tumor image is due to different edge threshold values.

More specifically, the image 4-1 is an example of a graph when the edge threshold value is B1. The image 4-2 is an example of a graph when the edge threshold value is B2. The value B2 is larger than the value B1. The image 4-3 is an example of a graph when the edge threshold value is B3. The value B3 is larger than the value B2. The image 4-4 is an example of a graph when the edge threshold value is B4. The value B4 is larger than the value B3. The image 4-5 is an example of a graph when the edge threshold value is B5. The value B5 is larger than the value B4.

FIG. 9 shows that the larger the edge threshold value, the more heterogeneous regions inside the tumor the obtained graph represents. A reason why the larger the edge threshold value, the more heterogeneous regions inside the tumor the graph represents is that as the edge threshold value increases, a graph is created by using only information of heterogeneous regions inside the tumor having a large difference in CT value. More specifically, a reason is as follows. That is, in the case of a graph having only edges whose weights are equal to or larger than the edge threshold value, a graph is obtained in which a difference between a weight of one vertex and a weight of the other vertex of two vertices connected by an edge is larger as the edge threshold value increases. The larger the difference between the weight of one vertex and the weight of the other vertex of the two vertices connected by the edge, the more heterogeneous an inside of the tumor represented by the graph. Therefore, the larger the edge threshold value, the more heterogeneous regions inside the tumor the obtained graph represents.

<Example of Graph Amount>

Figure 10:
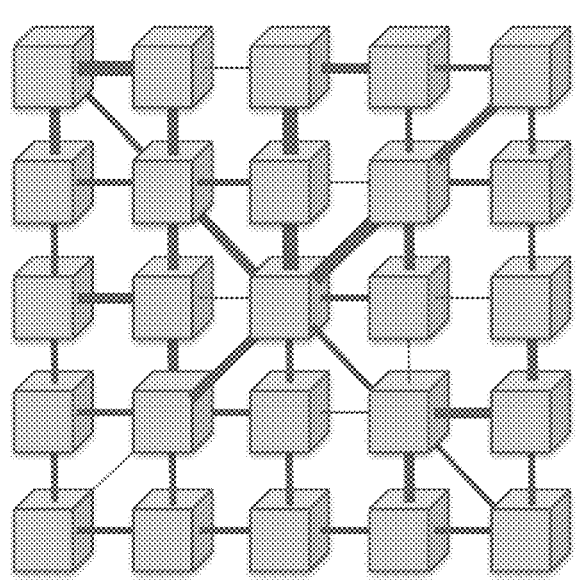
FIG. 10 is a first diagram showing an example of a graph amount according to the embodiment.

An example of a graph amount will be described in more detail. FIG. 10 is a first diagram showing an example of the graph amount according to the embodiment. FIG. 10 shows a graph having 25 vertices in total. The graph in FIG. 10 is a graph having a topology in which 25 vertices are arranged in a 5×5 matrix. The graph in FIG. 10 is a weighted graph, and a thickness of the edge indicates the weight of the edge. The thicker the edge, the heavier the weight of the edge.

The graph amount may be, for example, an amount related to a vertex. The amount related to the vertex is, for example, the number of vertices of the graph. In the example of FIG. 10, a value of the graph amount indicating the number of vertices is 25. Hereinafter, the number of vertices of the graph is referred to as a 1st graph feature.

The graph amount may be, for example, an amount related to an edge. The amount related to the edge is, for example, the number of edges of the graph. The edge of the graph satisfies a condition that a difference between pixel index values of two vertices connected by the edge satisfies a difference condition. The edge of the graph satisfies a condition that an absolute value of a difference between pixel values of two vertices connected by the edge is equal to or larger than the edge threshold value, for example.

Hereinafter, for simplification of description, the prognosis prediction system 100 will be described by taking, as an example, a case where the edge of the graph satisfies the condition that an absolute value of a difference between pixel values of two vertices connected by the edge is equal to or larger than the edge threshold value. Hereinafter, the number of edges of the graph is referred to as a 2nd graph feature.

The amount related to the edge may be, for example, a total value of weights of the edges of the graph. Hereinafter, the total value of the weights of the edges of the graph is referred to as a 3rd graph feature. The amount related to the edge may be, for example, an average value in the graph of weights of the edges of the graph. Hereinafter, the average value in the graph of the weights of the edges of the graph is referred to as a 4th graph feature. The amount related to the edge may be, for example, a maximum value in the graph of weights of the edges of the graph. Hereinafter, the maximum value in the graph of the weights of the edges of the graph is referred to as a 5th graph feature.

The amount related to the edge may be, for example, of the edges in the graph, the number of edges whose difference between the weight and an edge threshold value is equal to or smaller than a predetermined difference. The condition that the difference between the weight and the edge threshold value is equal to or smaller than the predetermined difference may be, for example, a condition that the weight is the same as the edge threshold value. Hereinafter, of the edges in the graph, the number of edges that satisfies the condition that the weight is the same as the edge threshold value is referred to as a 6th graph feature.

The amount related to the edge may be, for example, of the edges in the graph, the number of edges whose difference between the weight and the edge threshold value is larger than a predetermined difference. The condition that the difference between the weight and the edge threshold value is larger than the predetermined difference may be, for example, a condition that the weight is larger than the edge threshold value. Hereinafter, of the edges in the graph, the number of edges that satisfies the condition that the weight is larger than the edge threshold value is referred to as a 7th graph feature.

The graph amount may be, for example, an amount related to a degree. The amount related to the degree is, for example, a total value of degrees in the graph. Hereinafter, the total value of the degrees in the graph is referred to as an 8th graph feature. The amount related to the degree may be, for example, an average value of the degrees in the graph. Hereinafter, the average value of the degrees in the graph is referred to as a 9th graph feature.

Figure 11:
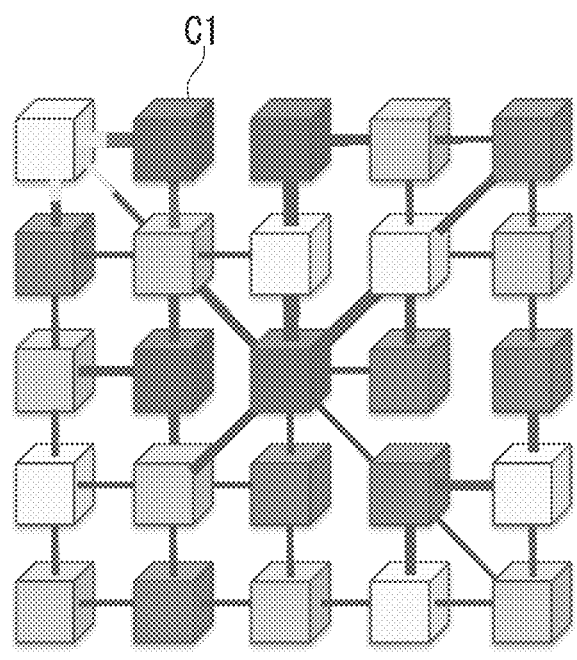
FIG. 11 is a second diagram showing an example of the graph amount according to the embodiment.

FIG. 11 is a second diagram showing an example of the graph amount according to the embodiment. FIG. 11 shows a graph having a 5×5 topology. FIG. 11 shows that the number of edges connected to a vertex C1 is two. Since two edges are connected to the vertex C1, a degree of the vertex C1 is 2. The two edges connected to the vertex C1 are edges of the graph.

As described above, the graph amount may be, for example, an amount related to the minimum spanning tree. The amount related to the minimum spanning tree is, for example, a total value of weights of edges of the minimum spanning tree. Hereinafter, the total value of the weights of the edges of the minimum spanning tree is referred to as a 10th graph feature. The amount related to the minimum spanning tree may be, for example, the number of edges of the minimum spanning tree. Hereinafter, the number of the edges of the minimum spanning tree is referred to as an 11th graph feature.

The amount related to the minimum spanning tree may be a weight of an edge having the maximum weight of the edges constituting the minimum spanning tree. Hereinafter, the weight of the edge having the maximum weight of the edges constituting the minimum spanning tree is referred to as a 12th graph feature. The amount related to the minimum spanning tree may be a ratio of the number of edges constituting the minimum spanning tree to the number of edges of the graph. Hereinafter, the ratio of the number of edges constituting the minimum spanning tree to the number of edges of the graph is referred to as a 13th graph feature.

The graph amount is not necessarily an amount obtained from one tumor image. The graph amount may be obtained from a plurality of images obtained by imaging the same tumor under different conditions. For example, the graph amount may be a total value of values of first-type individual graph amounts. A first-type individual graph amount is a predefined graph amount obtained based on a plurality of cross-sectional views. The plurality of cross-sectional views are cross-sectional views of the same tumor, for example, cross-sectional views at different positions in a predetermined direction. The predetermined direction is, for example, an axial direction. Hereinafter, the total value of the values of the first-type individual graph amounts is referred to as a 14th graph feature.

The graph amount may be, for example, an amount obtained by dividing the total value of the values of the first-type individual graph amounts by a volume of the tumor. Hereinafter, the amount obtained by dividing the total value of the values of the first-type individual graph amounts by the volume of the tumor is referred to as a 15th graph feature. The graph amount may be, for example, an amount obtained by dividing the total value of the values of the first-type individual graph amounts by the number of cross-sectional views. Hereinafter, the amount obtained by dividing the total value of the values of the first-type individual graph amounts by the number of cross-sectional views is referred to as a 16th graph feature.

The graph amount may be, for example, an amount related to a three-dimensional graph (that is, a spatial graph) obtained as a result of connecting graphs obtained for a plurality of cross-sectional views by edges. The plurality of cross-sectional views are cross-sectional views of the same tumor, for example, cross-sectional views at different positions in a predetermined direction. The predetermined direction is, for example, an axial direction. Hereinafter, the amount related to the three-dimensional graph obtained as the result of connecting graphs obtained for a plurality of cross-sectional views by edges is referred to as a 17th graph feature.

The plurality of cross-sectional views need not necessarily be cross-sectional views having different spatial positions, and may be cross-sectional views having different temporal positions. That is, the plurality of cross-sectional views may be results obtained by imaging the same cross section at a plurality of different times.

The plurality of cross-sectional views may be cross-sectional views in which spatial positions and temporal positions are different.

The graph amount is not necessarily an amount obtained from one graph. The graph amount may be an amount obtained based on a second-type individual graph amount. The second-type individual graph amount is a set of predefined graph amounts obtained from a plurality of graphs indicating the same tumor image and having different edge threshold values.

The graph amount is, for example, a slope of a function indicating a relationship between an edge threshold value of a graph ordered set and a value of each element. The graph ordered set is an ordered set in which elements in the second-type individual graph amount are arranged in an order of a magnitude of edge threshold values. Hereinafter, the slope of the function indicating the relationship between the edge threshold value of the graph ordered set and the value of each element is referred to as an 18th graph feature.

FIG. 12 is a third diagram showing an example of the graph amount according to the embodiment. More specifically, FIG. 12 is a diagram showing an example of the second-type individual graph amount. In FIG. 12, a horizontal axis represents an edge threshold value, and a vertical axis represents a value of a graph amount. An ordered set of values of the vertical axis corresponding to edge threshold values in a curve L1 in FIG. 12 is an example of the graph ordered set. That is, the curve L1 in FIG. 12 is a line representing an example of the graph ordered set. The edge threshold value was 1 HU at minimum and 50 HU at maximum. As the edge threshold value, 50 values separated by 1 HU intervals from 1 HU to 50 HU were used.

The graph amount may be, for example, a value of a y-intercept of the function indicating the relationship between the edge threshold value of the graph ordered set and the value of each element. Hereinafter, the value of the y-intercept of the function indicating the relationship between the edge threshold value of the graph ordered set and the value of each element is referred to as a 19th graph feature.

The graph amount may be, for example, a position of a peak of the function indicating the relationship between the edge threshold value of the graph ordered set and the value of each element. Specifically, the position of the peak is the edge threshold value corresponding to a value of the peak of the function indicating the relationship between the edge threshold value of the graph ordered set and the value of each element. Hereinafter, the position of a peak of the function indicating the relationship between the edge threshold value of the graph ordered set and the value of each element is referred to as a 20th graph feature.

The graph amount may be, for example, a kurtosis of the function indicating the relationship between the edge threshold value of the graph ordered set and the value of each element. Hereinafter, the kurtosis of the function indicating the relationship between the edge threshold value of the graph ordered set and the value of each element is referred to as a 21th graph feature.

The graph amount may be, for example, a skewness of the function indicating the relationship between the edge threshold value of the graph ordered set and the value of each element. Hereinafter, the skewness of the function indicating the relationship between the edge threshold value of the graph ordered set and the value of each element is referred to as a 22th graph feature.

The graph amount may be, for example, an interquartile range of the function indicating the relationship between the edge threshold value of the graph ordered set and the value of each element. Hereinafter, the interquartile range of the function indicating the relationship between the edge threshold value of the graph ordered set and the value of each element is referred to as a 23th graph feature.

Experimental Result

An example of a result of an experiment of prediction of prognosis using the prognosis prediction system 100 will be described. Cases used in the experiment were non-small cell lung cancer cases in total of 304 cases excluding cases corresponding to excluded items among patients subjected to radiation therapy of lung cancer. That is, a total of 304 tumor images were used in the experiment. Each of the tumor images used in the experiment was a planned CT image or structure data. Cases of excluded items were cases of small cell lung cancer, cases of unknown histology, and cases of insufficient GTV contour.

In the experiment, 70% of the total 304 tumor images were used to train a training model. That is, 213 cases, which is 70% of the total of 304 tumor images, were used as information in training data. In the experiment, 91 cases, which is 30% of the total of 304 tumor images, were used to verify accuracy of prediction of the learned training model. That is, 30% of the total 304 tumor images were used as test data. A ratio of tumor images of dead patients to tumor images of patients who did not die among tumor images used for learning was substantially the same as a ratio of tumor images of dead patients to tumor images of patients who did not die among tumor mages used for verification.

FIG. 13 is a first diagram showing an experiment according to the embodiment. More specifically, FIG. 13 is a diagram showing details of cases used in the experiment. FIG. 13 shows that cases of 304 patients were used in the experiment. FIG. 13 shows that a median value of a survival period of the patient was 598 days. FIG. 13 shows that a range of the survival period of the patient was 1 day to 3364 days.

FIG. 13 shows a histologic distribution of 304 patients. FIG. 13 shows that histology was adenocarcinoma for 135 persons among 304 persons. FIG. 13 shows that histology was squamous cell carcinoma for 149 persons among 304 persons. FIG. 13 shows that histology was large cell carcinoma for 7 persons among 304 persons. FIG. 13 shows that histology was NOS (not otherwise specified) for 13 persons among 304 persons.

FIG. 13 shows that survival periods of patients whose histology is adenocarcinoma had a median value of 562 days and a range of 1 day to 3364 days. FIG. 13 shows that survival periods of patients whose histology is squamous cell carcinoma had a median value of 775 days and a range of 8 days to 3253 days. FIG. 13 shows that survival periods of patients whose histology is large cell carcinoma had a median value of 540 days and a range of 279 days to 2875 days. FIG. 13 shows that survival periods of patients whose histology is NOS had a median value of 967 days and a range of 77 days to 2562 days.

FIG. 13 shows a distribution of disease stages of 304 patients. FIG. 13 shows that there are 83 patients having stage I disease. FIG. 13 shows that there are 25 patients having stage II disease. FIG. 13 shows that there are 146 patients having stage III disease. FIG. 13 shows that there are 41 patients having stage IV disease.

FIG. 13 shows that survival periods of patients whose disease stage is stage I had a median value of 895 days and a range of 10 days to 3364 days. FIG. 13 shows that survival periods of patients whose disease stage is stage II had a median value of 418 days and a range of 49 days to 2875 days. FIG. 13 shows that survival periods of patients whose disease stage is stage III had a median value of 677.5 days and a range of 19 days to 3302 days. FIG. 13 shows that survival periods of patients whose disease stage is stage IV had a median value of 208 days and a range of 9 days to 2824 days.

Figure 14:
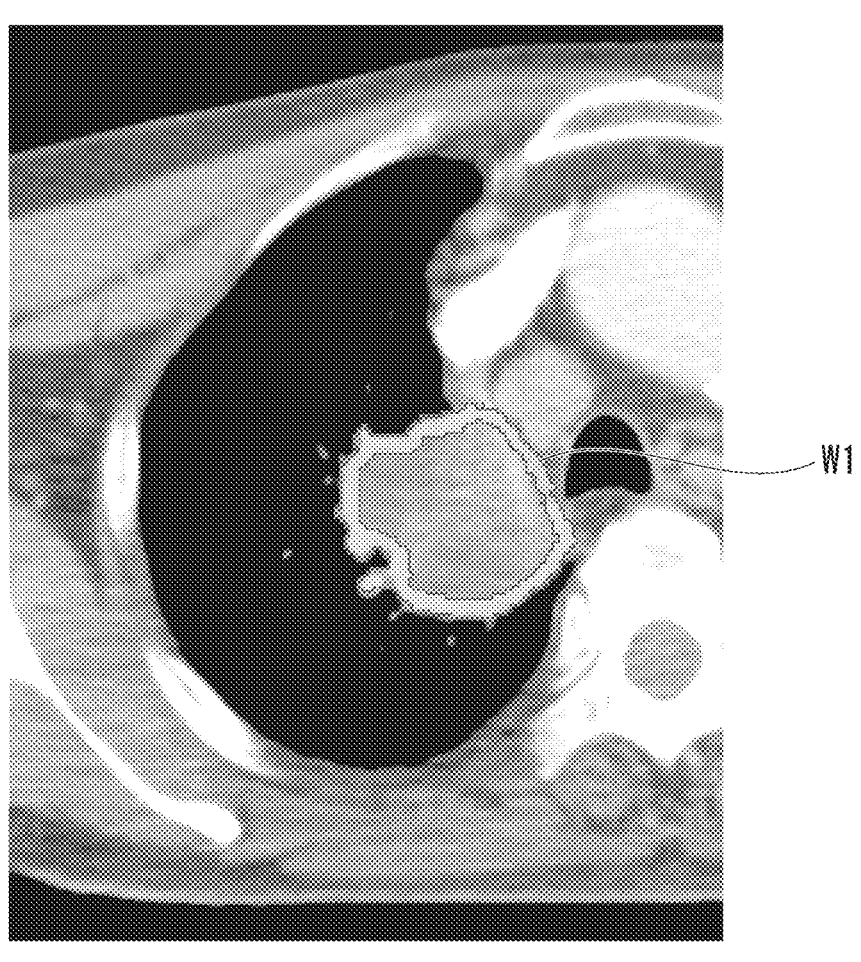
FIG. 14 is a second diagram showing an experiment according to the embodiment.

FIG. 14 is a second diagram showing an experiment according to the embodiment. More specifically, FIG. 14 is a diagram showing an example of a tumor image used in the experiment. In the experiment, a gross tumor volume (GTV) region was extracted from a planned CT image used in a treatment plan, and graph tumor information was generated for an image of the extracted GTV region. That is, in the experiment, the image of the GTV region in the planned CT image was used as the tumor image. A region surrounded by a frame W1 in FIG. 14 is an example of the image of the GTV region.

Figure 15:
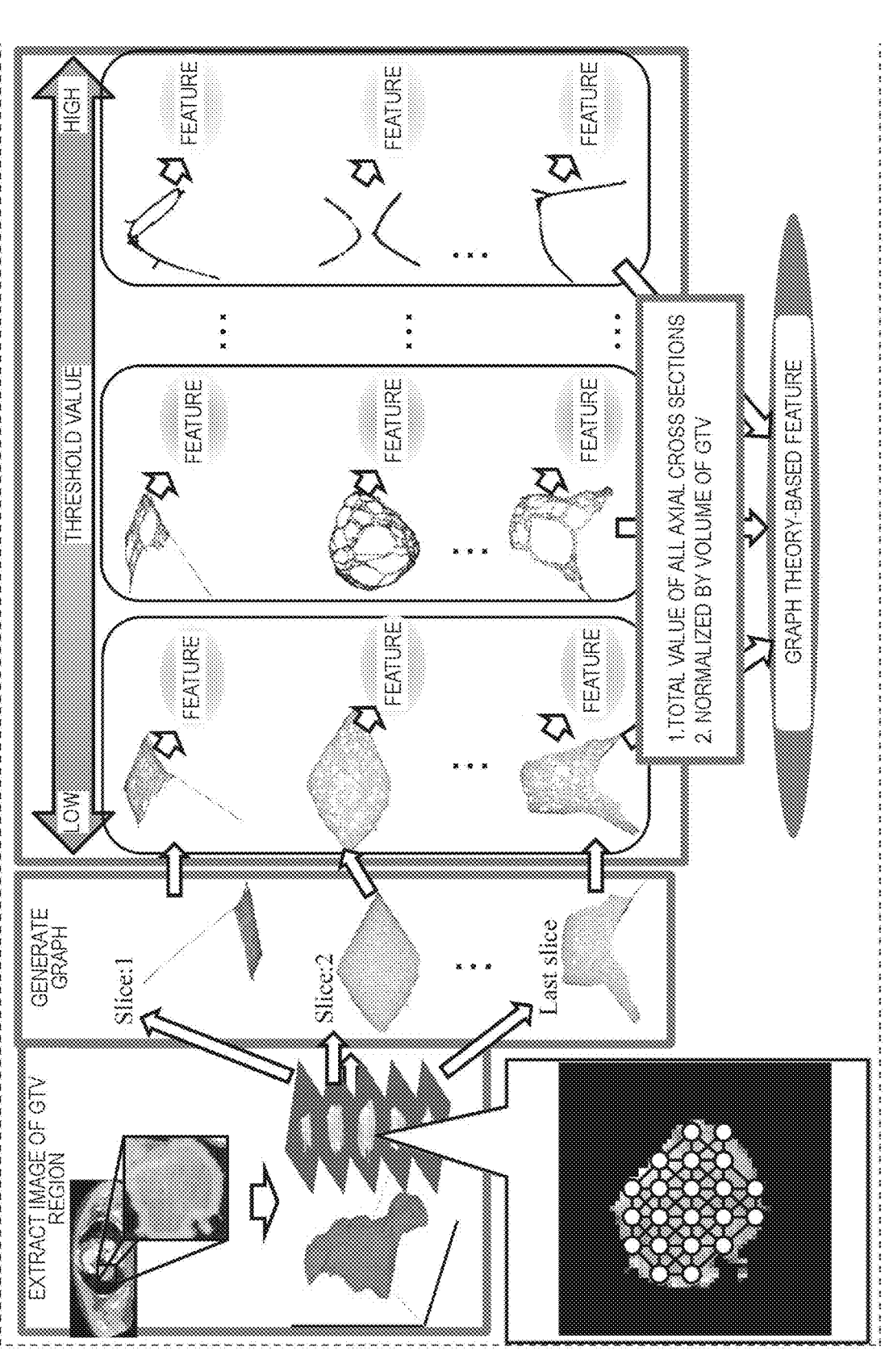
FIG. 15 is a third diagram showing an experiment according to the embodiment.

FIG. 15 is a third diagram showing an experiment according to the embodiment. More specifically, FIG. 15 is a diagram showing an outline of an example of a flow of processing performed in the experiment until graph tumor information is generated based on the tumor image. In the experiment, a plurality of cross-sectional views of the patient were acquired. The cross-sectional view was an axial cross-sectional view. In the experiment, an image of the GTV region was extracted for each of the acquired cross-sectional views.

"Slice: 1" in FIG. 15 means a first cross-sectional view. "Slice: 2" in FIG. 15 means a second cross-sectional view. "Last Slice" shown in FIG. 15 means a last cross-sectional view of the plurality of cross-sectional views. In a case of FIG. 15, the number of cross-sectional views was 20. Therefore, "Last Slice" in FIG. 15 means a 20th cross-sectional view.

In the experiment, a graph was generated for each image of the GTV region. In the experiment, a predetermined threshold value was set for an edge indicated by the graph. In the experiment, processing of removing an edge less than the set predetermined threshold value was executed. If the edge less than the predetermined threshold value is removed, the graph tumor information indicates heterogeneity inside the tumor with higher accuracy than if the edge is not removed.

In the experiment, there were a plurality of threshold values used to remove the edge. Specifically, the edge threshold value used in the experiment was 5 HU at the minimum and 50 HU at the maximum. As the edge threshold value used in the experiment, 10 values separated by 5 HU intervals from 5 HU to 50 HU were used. In the experiment, processing of acquiring a value of the graph amount for each threshold value was executed on the image of the GTV region. Hereinafter, processing of executing the processing of acquiring the value of the graph amount for each threshold value for the image of the GTV region is referred to as first-stage graph amount acquisition processing.

In the experiment, processing of acquiring a sum of graph amounts acquired in the first-stage graph amount acquisition processing and dividing the sum by a volume of the GTV was executed. Hereinafter, processing of acquiring the sum of the graph amounts acquired in the first-stage graph amount acquisition processing and dividing the sum by the volume of the GTV is referred to as second-stage graph amount acquisition processing.

In the experiment, a graph amount acquired in the first-stage graph amount acquisition processing and a graph amount acquired in the second-stage graph amount acquisition processing were used. In the experiment, a total of 127 graph amounts were used.

The total of 127 graph amounts were amounts classified into any one of a total of 37 classifications, which are specifically the 14th graph feature obtained based on the 1st graph feature, the 15th graph feature obtained based on the 2nd graph feature to the 12th graph feature, (18-1)th graph feature to (18-13)th graph feature, (19-1)th graph feature to (19-0)th graph feature, the 20th graph feature in which each element in the second-type individual graph amount is the 10th graph feature, and the 21th graph feature in which each element in the second-type individual graph amount is the 10th graph feature.

The (18-1)th graph feature to (18-13)th graph feature and the (19-1)th graph feature to (19-10)th graph feature will be described later. In the experiment, information indicating each value of the 127 graph amounts thus obtained was used as the graph tumor information.

A reason why a total number of the graph amounts used in the experiment is a value larger than 23, such as 127 or 159, although 37 types of graph amounts are used in the experiment will be described. A reason for this is that the graph amount used in the experiment was not necessarily one for each type of classification. For example, in the experiment, for some of the 37 types of classifications, graph amounts were obtained for a plurality of edge threshold values. In the experiment, the number of edge threshold values was 10. For a part of the 37 types of classifications in the experiment, graph amounts were acquired for each cross-sectional view.

A reason will be described more specifically by taking a case where the number of cross sections is one as an example. In the experiment, the number of 1st graph features was 1 regardless of the edge threshold value. Therefore, a total number of graph amounts related to the vertices was 1. The 2nd graph feature to the 4th graph feature were acquired for each edge threshold value. The number of 5th graph features was 1 regardless of the edge threshold value. The 6th graph feature and the 7th graph feature were acquired for each edge threshold value. Since the number of edge threshold values was 10, a total number of graph amounts related to the edge was 51.

The 8th graph feature and the 9th graph feature were acquired for each edge threshold value. Therefore, a total number of graph amounts related to the degree was 20. The 10th graph feature to the 13th graph feature were acquired for each edge threshold value. Therefore, the number of graph amounts related to the degree was 40.

The 14th graph feature was acquired for the 1st graph feature. The 15th graph feature is acquired for each edge threshold value.

The 18th graph feature is acquired for each 15th graph feature. The 19th graph feature is acquired for each 15th graph feature. The 20th graph feature was acquired from the 15th graph feature obtained based on the 10th graph feature. The 21th graph feature was acquired from the 15th graph feature obtained based on the 10th graph feature. The 22th graph feature was acquired from the 15th graph feature obtained based on the 10th graph feature.

In the experiment, verification was performed in advance using a LASSO-cox regression model to determine how many types of graph amounts are preferably used. As a result, it was confirmed that, by using the above total of 127 graph amounts among the total of 159 graph amounts to be verified, prediction accuracy equal to or higher than that in a case of using 128 or more graph amounts can be obtained. In addition to the total of 127 graph amounts described above, graph amounts to be verified include the 15th graph feature obtained based on the 13th graph feature, an 18th graph feature in which each element in the second-type individual graph amount is the 2nd graph feature and a slope is a slope of a third-order term, an 18th graph feature in which each element in the second-type individual graph amount is the 2nd graph feature and the slope is a slope of a second-order term, an 18th graph feature in which each element in the second-type individual graph amount is the 7th graph feature and the slope is the slope of the third-order term, an 18th graph feature in which each element in the second-type individual graph amount is the 7th graph feature and the slope is the slope of the second-order term, an 18th graph feature in which each element in the second-type individual graph amount is the 6th graph feature and the slope is the slope of the third-order term, an 18th graph feature in which each element in the second-type individual graph amount is the 6th graph feature and the slope is the slope of the second-order term, an 18th graph feature in which each element in the second-type individual graph amount is the 6th graph feature and the slope is a slope of a first-order term, an 18th graph feature in which each element in the second-type individual graph amount is the 4th graph feature and the slope is the slope of the third-order term, an 18th graph feature in which each element in the second-type individual graph amount is the 4th graph feature and the slope is the slope of the second-order term, an 18th graph feature in which each element in the second-type individual graph amount is the 3rd graph feature and the slope is the slope of the first-order term, an 18th graph feature in which each element in the second-type individual graph amount is the 9th graph feature and the slope is the slope of the third-order term, an 18th graph feature in which each element in the second-type individual graph amount is the 9th graph feature and the slope is the slope of the second-order term, an 18th graph feature in which each element in the second-type individual graph amount is the 8th graph feature and the slope is the slope of the third-order term, an 18th graph feature in which each element in the second-type individual graph amount is the 8th graph feature and the slope is the slope of the second-order term, an 18th graph feature in which each element in the second-type individual graph amount is the 13th graph feature and the slope is the slope of the third-order term, an 18th graph feature in which each element in the second-type individual graph amount is the 13th graph feature and the slope is the slope of the second-order term, an 18th graph feature in which each element in the second-type individual graph amount is the 13th graph feature and the slope is the slope of the first-order term, a 19th graph feature in which each element in the second-type individual graph amount is the 13th graph feature, an 18th graph feature in which each element in the second-type individual graph amount is the 12th graph feature and the slope is the slope of the third-order term, an 18th graph feature in which each element in the second-type individual graph amount is the 12th graph feature and the slope is the slope of the second-order term, an 18th graph feature in which each element in the second-type individual graph amount is the 12th graph feature and the slope is the slope of the first-order term, and the 22th graph feature in which each element in the second-type individual graph amount is the 10th graph feature.

In the experiment, training using the LASSO-cox regression model as the training model was performed. In the experiment, a pair of graph tumor information and prognosis information acquired in the processing shown in FIG. 15 was used as the training data set for the training. The prognosis information in the experiment was survival-death information and a survival period.

Thus, in the experiment, the prognosis prediction information was acquired by updating the LASSO-cox regression model by training in which the explanatory variable was the graph tumor information acquired in the processing shown in FIG. 15 and the objective variable was the prognosis information. Therefore, prognosis prediction information in the experiment was information indicating a relationship between the graph tumor information and the prognosis acquired in the processing shown in FIG. 15. In the training performed in the experiment, specifically, a coefficient is optimized for each graph amount. The LASSO-cox regression model is therefore an example of the prognosis prediction training model.

With reference to FIGS. 16 to 19, training in the prognosis prediction system 100 will be described in comparison with the technique in the related art. The technique in the related art to be compared is a technique for predicting prognosis using 107 radiomics features.

14 features among the 107 radiomics features in the technique in the related art to be compared are features representing a shape or size of a tumor. 18 features among the 107 radiomics features in the technique in the related art to be compared are features representing a distribution of pixel values of the tumor. 75 features among the 107 radiomics features in the technique in the related art to be compared are features representing non-uniformity of the tumor.

More specifically, among features of the technique in the related art to be compared, the feature representing the shape or size of the tumor is a feature generally referred to as shape. Among the features of the technique in the related art to be compared, the feature representing the distribution of the pixel values of the tumor is a feature generally referred to as statistical. Among the features of the technique in the related art to be compared, the feature representing the non-uniformity of the tumor is a feature generally referred to as texture.

The technique in the related art to be compared is a technique of updating a training model by a machine learning method to acquire a learned training model indicating a relationship between the 107 radiomics features and a prognosis. The technique in the related art to be compared is a technique for predicting a prognosis using the learned training model obtained by training. Hereinafter, the training model in the technique in the related art to be compared is referred to as a comparison training model.

Figure 16:
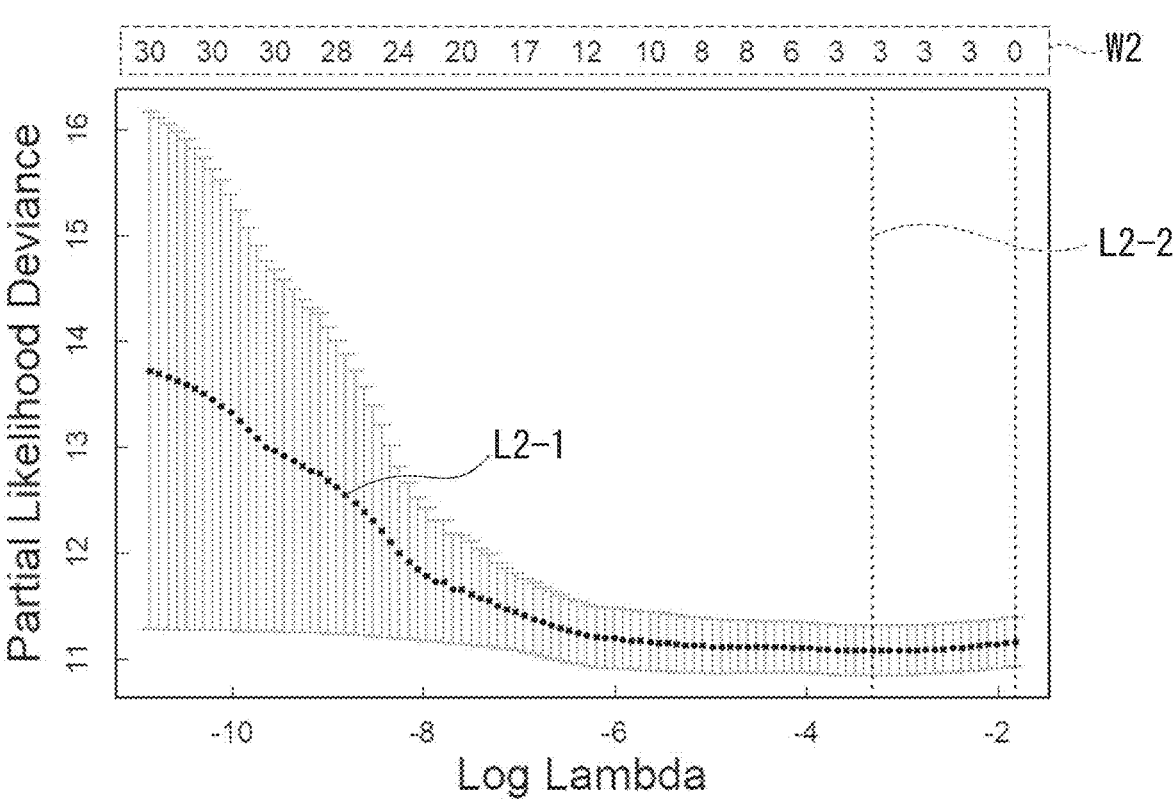
FIG. 16 is a fourth diagram showing an experiment according to the embodiment.

FIG. 16 is a fourth diagram showing an experiment according to the embodiment. More specifically, FIG. 16 is a first diagram showing an example of a result of inputting training data into the prognosis prediction training model of the prognosis prediction system 100 and training the prognosis prediction training model. A vertical axis in FIG. 16 indicates a partial likelihood deviance of a conditional probability. A horizontal axis in FIG. 16 indicates log lambda. The log lambda means a parameter used for model optimization. The parameter used for the model optimization specifically means a regularization coefficient.

FIG. 16 shows the partial likelihood deviance of the conditional probability for each value on the horizontal axis. A line L2-1 in FIG. 16 indicates a result obtained by minimizing an error in a result of prognosis prediction by the prognosis prediction system 100. A line L2-2 in FIG. 16 indicates a regularization coefficient that minimizes the error in the result of the prognosis prediction by the prognosis prediction system 100. The error in the result of the prognosis prediction is a degree of error in the result of the prognosis prediction. Each numerical value surrounded by a frame W2 in FIG. 16 means a regularization coefficient.

Figure 17:
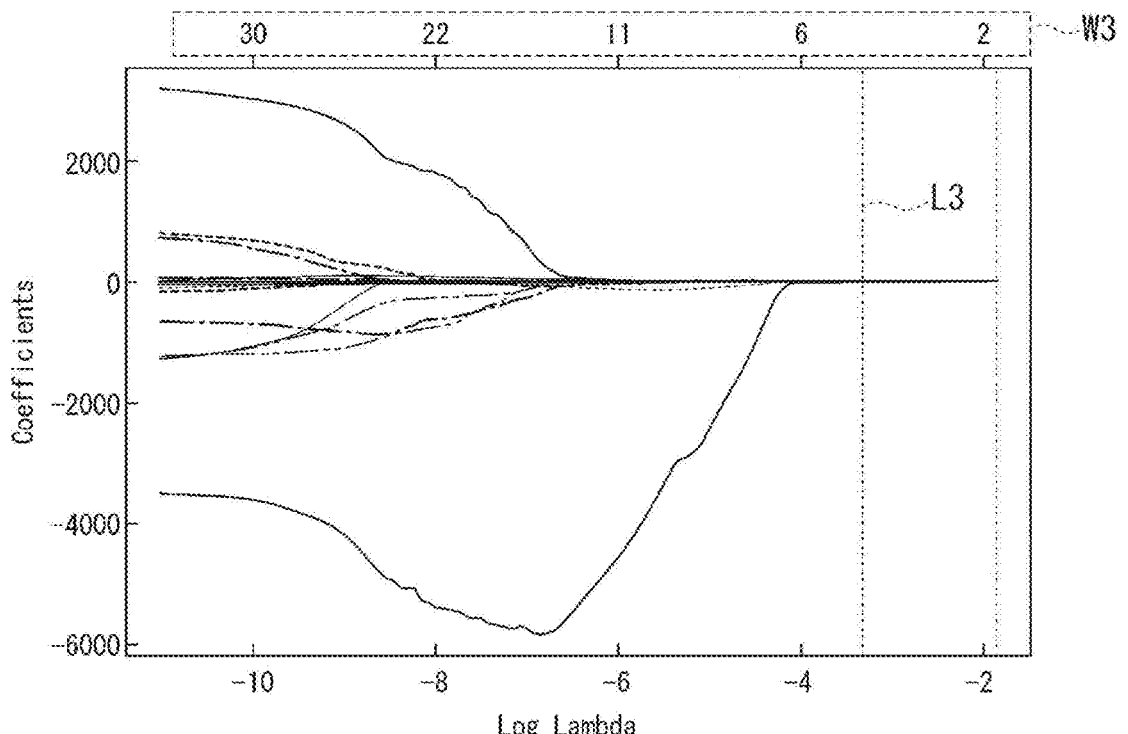
FIG. 17 is a fifth diagram showing an experiment according to the embodiment.

FIG. 17 is a fifth diagram showing an experiment according to the embodiment. More specifically, FIG. 17 is a second diagram showing an example of a result of inputting the training data into the prognosis prediction training model of the prognosis prediction system 100 and training the prognosis prediction training model. A vertical axis in FIG. 17 indicates coefficients. Specifically, the coefficient is a coefficient used for calculating a rad score. The rad score is an index indicating a prognosis. A higher value of a rad score indicates a worse prognosis. A horizontal axis in FIG. 17 indicates log lambda. The log lambda means a parameter used for model optimization. The parameter used for the model optimization specifically means a regularization coefficient. That is, FIG. 17 shows a relationship between each feature and regularization. Features in the experiment and in the prognosis prediction system 100 are a total of 159 graph amounts.

The feature in the prognosis prediction system 100 may be any amount as long as the amount is a graph amount representing graph tumor information. Therefore, features in the prognosis prediction system 100 may be, for example, the 1st graph feature to the 22th graph feature described above or later. In the example of FIG. 17, the features in the prognosis prediction system 100 are the total of 159 graph amounts described above. Thus, the feature in the prognosis prediction system 100 may be any amount as long as the amount is a graph amount representing graph tumor information, and the feature in the prognosis prediction system 100 to be used may be an amount defined according to an application situation of the prognosis prediction system 100.

A line L3 in FIG. 17 indicates a regularization coefficient that minimizes the error in the result of the prognosis prediction by the prognosis prediction system 100. Each numerical value surrounded by a frame W3 in FIG. 17 means a regularization coefficient. Each graph in FIG. 17 shows a coefficient of a graph amount input to the prognosis prediction training model. Therefore, even if graphs have the same color scheme or line type (that is, even if graphs exist on the same line), each point on the horizontal axis indicates a different coefficient of a graph amount.

Figure 18:
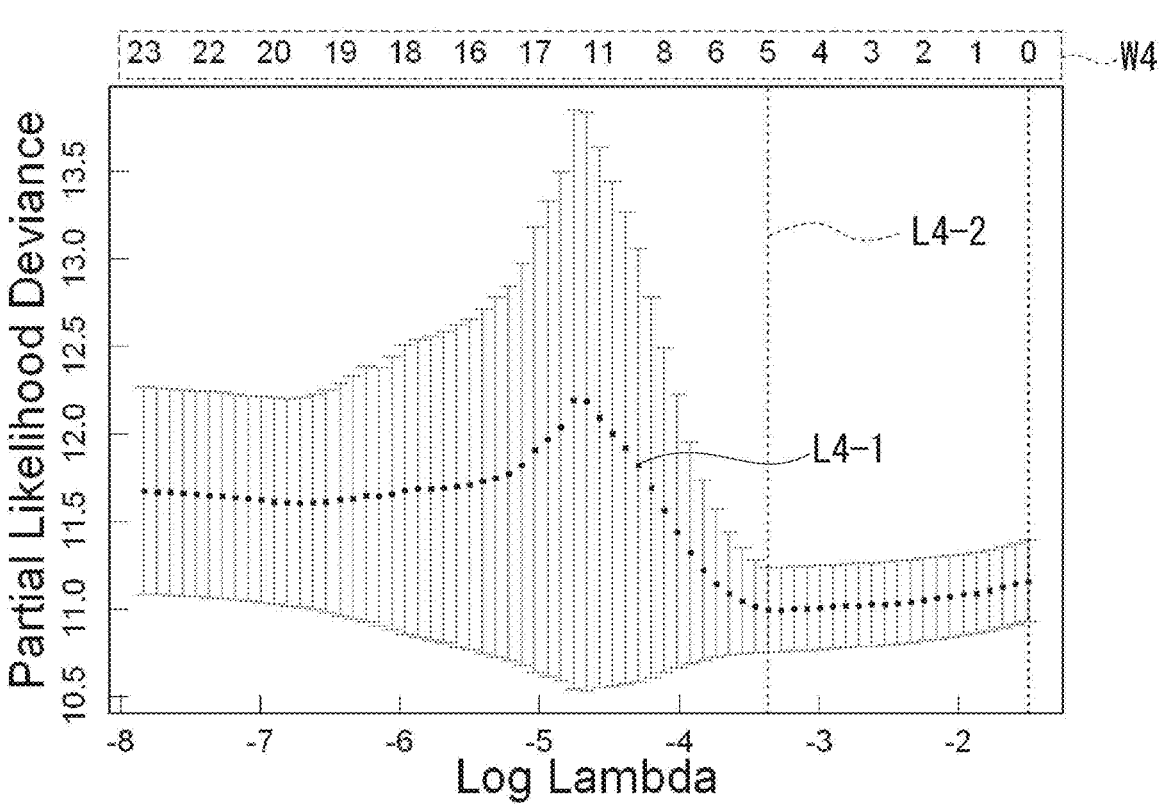
FIG. 18 is a sixth diagram showing an experiment according to the embodiment.

FIG. 18 is a sixth diagram showing an experiment according to the embodiment. More specifically, FIG. 18 is a first diagram showing an example of a result of training a comparison training model by inputting training data to the comparison training model in the technique in the related art. A vertical axis in FIG. 18 indicates a partial likelihood deviance of a conditional probability. A horizontal axis in FIG. 18 indicates log lambda. The log lambda means a regularization coefficient.

FIG. 18 shows the partial likelihood deviance of the conditional probability for each value on the horizontal axis. A dotted line L4-1 in FIG. 18 indicates a result obtained by minimizing an error in a result of prognosis prediction by the learned comparison training model. A line L4-2 in FIG. 18 indicates a regularization coefficient that minimizes the error in the result of the prognosis prediction by the learned comparison training model. Each numerical value surrounded by a frame W4 in FIG. 18 means a regularization coefficient.

Figure 19:
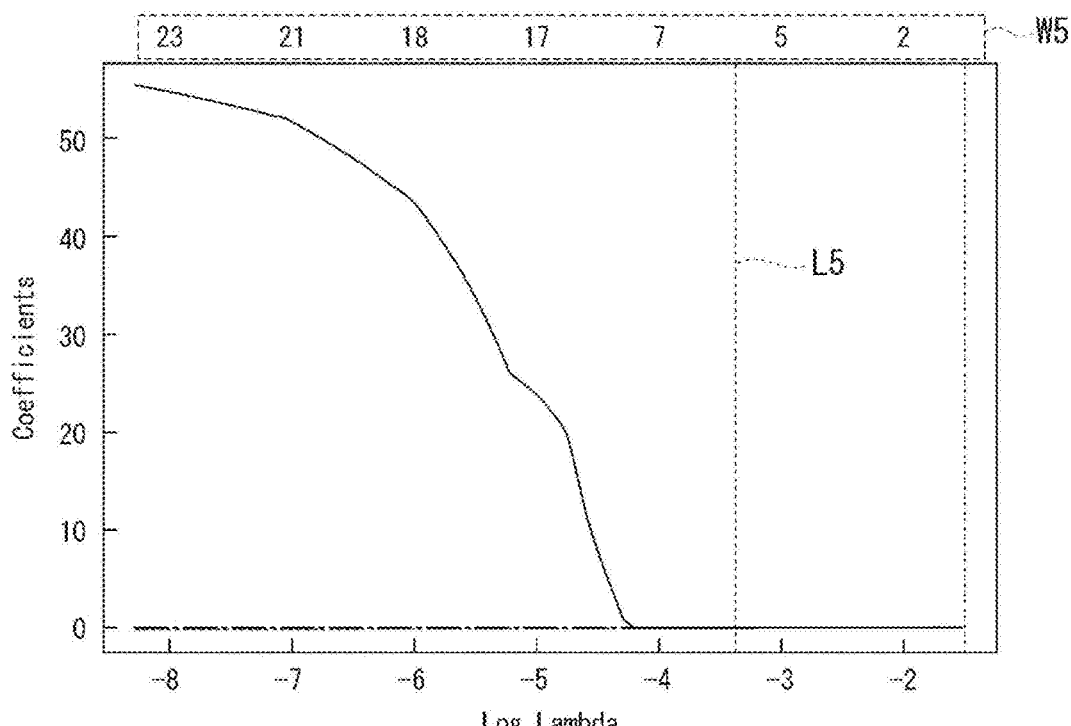
FIG. 19 is a seventh diagram showing an experiment according to the embodiment.

FIG. 19 is a seventh diagram showing an experiment according to the embodiment. More specifically, FIG. 19 is a second diagram showing an example of a result of training a comparison training model by inputting training data to the comparison training model in the technique in the related art. A vertical axis in FIG. 19 indicates coefficients. Specifically, the coefficient is coefficient used for calculating a rad score. A horizontal axis in FIG. 19 indicates log lambda. The log lambda means a regularization coefficient.

A line L5 in FIG. 19 indicates a regularization coefficient that minimizes an error in a result of prognosis prediction by the learned comparison training model. Each numerical value surrounded by a frame W5 in FIG. 19 means a regularization coefficient. Each graph in FIG. 19 shows a coefficient of a graph amount input to the prognosis prediction training model. Therefore, even if graphs have the same color scheme or line type (that is, even if graphs exist on the same line), each point on the horizontal axis indicates a different coefficient of a graph amount.

The results of FIGS. 16 and 17 and the results of FIGS. 18 and 19 indicate that the error of the result of the prognosis prediction by the prognosis prediction system 100 converges more than the error of the result of the prognosis prediction by the technique in the related art. Since the error of the result of the prognosis prediction by the prognosis prediction system 100 converges more than the error of the result of the prognosis prediction by the technique in the related art, the prognosis prediction system 100 is more useful than the technique in the related art.

FIG. 20 is an eighth diagram showing an experiment according to the embodiment. A row of "feature of graph theory" in a table of FIG. 20 indicates information related to the graph amount used in the prognosis prediction system 100 in the experiment. A row of "feature in related art" in the table of FIG. 20 indicates information related to the radiomics feature used in the technique in the related art in the experiment. A column of "selected feature" in the table of FIG. 20 indicates a feature (graph amount) selected by the prognosis prediction system 100 in the experiment and a feature selected by the comparison training model. A column of "coefficient" in the table of FIG. 20 indicates each weight of a feature selected in the trained prognosis prediction training model used in the experiment and each weight of a feature selected in the trained comparison training model used in the experiment.

"Vertex number of vertices" in FIG. 20 means that the graph amount is the 1st graph feature. "Edge_number of edges having the same value as threshold value_threshold value 10" in FIG. 20 means that the graph amount is the 6th graph feature. "Histogram_number of edges having the same value as threshold value_approximate curve y-intercept" in FIG. 20 means that the graph amount is the 19th graph feature in which each element in the second-type individual graph amount is the 2nd graph feature. The table in FIG. 20 shows that a weight of graph amount for the "vertex number of vertices" was $5.259 \times 10\text{-}6$. The table in FIG. 20 shows that the weight of the graph amount for the "edge_number of edges having the same value as threshold value_threshold value 10" was $9.591 \times 10\text{-}2$. The table in FIG. 20 shows that the weight of the graph amount for the "histogram_number of edges having the same value as threshold value_approximate curve y-intercept" is 3.532.

The table of FIG. 20 shows that a weight of Maximum2DDiameterRow/shape was $9.924 \times 10\text{-}3$. The table of FIG. 20 shows that a weight of ZoneVariance/glszm was $1.917 \times 10\text{-}7$. The table of FIG. 20 shows that a weight of Complexity/ngtdm was $7.173 \times 10\text{-}5$. A definition of Maximum2DDiameterRow/shape is a maximum pairwise Euclidean distance between vertices on a tumor surface in a sagittal plane. A definition of ZoneVariance/glszm is a variation in size of adjacent voxels with the same pixel value. A definition of Complexity/ngtdm is a complexity of a matrix that digitizes a difference in average gradation value between a certain gradation value and adjacent gradation values within a certain distance.

FIGS. 21 and 22 show an example of a tumor image having a relatively good prognosis and an example of a tumor image having a relatively poor prognosis.

FIG. 21 is a ninth diagram showing an experiment according to the embodiment. More specifically, FIG. 21 is a diagram showing an example of an image of a tumor having a better prognosis than a tumor shown in FIG. 22. FIG. 21 shows an image G5 and an image G6. The image G5 is a diagram showing an example of the image of the tumor having a better prognosis than the tumor shown in FIG. 22. The image G6 is an example of a graph of the tumor shown in the image G5.

In the experiment, a rad score for the tumor shown in the image G5 obtained by the prognosis prediction system 100 was 0.45. On the other hand, in the experiment, a rad score for the tumor shown in the image G5 obtained by the technique in the related art was 0.94.

FIG. 22 is a tenth diagram showing an experiment according to the embodiment. More specifically, FIG. 22 is a diagram showing an example of an image of the tumor having a worse prognosis than the tumor shown in FIG. 21. FIG. 22 shows an image G7 and an image G8. The image G7 is a diagram showing an example of the image of the tumor having a worse prognosis than the tumor shown in FIG. 21. The image G8 is an example of a graph of the tumor shown in the image G7.

In the experiment, a rad score for the tumor shown in the image G7 obtained by the prognosis prediction system 100 was 0.80. 0.80 is 1.8 times of 0.45. On the other hand, in the experiment, a rad score for the tumor shown in the image G7 obtained by the technique in the related art was 1.08. 1.08 is 1.1 times of 0.94. As described above, in the experiment, the rad score obtained by the prognosis prediction system 100 more clearly indicates a change in a state of the tumor than the rad score obtained by the technique in the related art.

FIGS. 21 and 22 show that an inside of the tumor having a relatively poor prognosis is more heterogeneous than the tumor having a relatively good prognosis. FIGS. 21 and 22 show that a density of edges in the graph is higher for a tumor having a relatively poor prognosis. Thus, FIGS. 21 and 22 show that a user of the prognosis prediction system 100 can visually estimate the prognosis by displaying the graph of the tumor.

Therefore, the output unit 25 in the prognosis prediction device 2 may display a graph of the subject tumor. When the output unit 25 displays the graph of the subject tumor, the prognosis prediction device 2 has an effect of allowing the user to visually estimate the prognosis.

Figure 23:
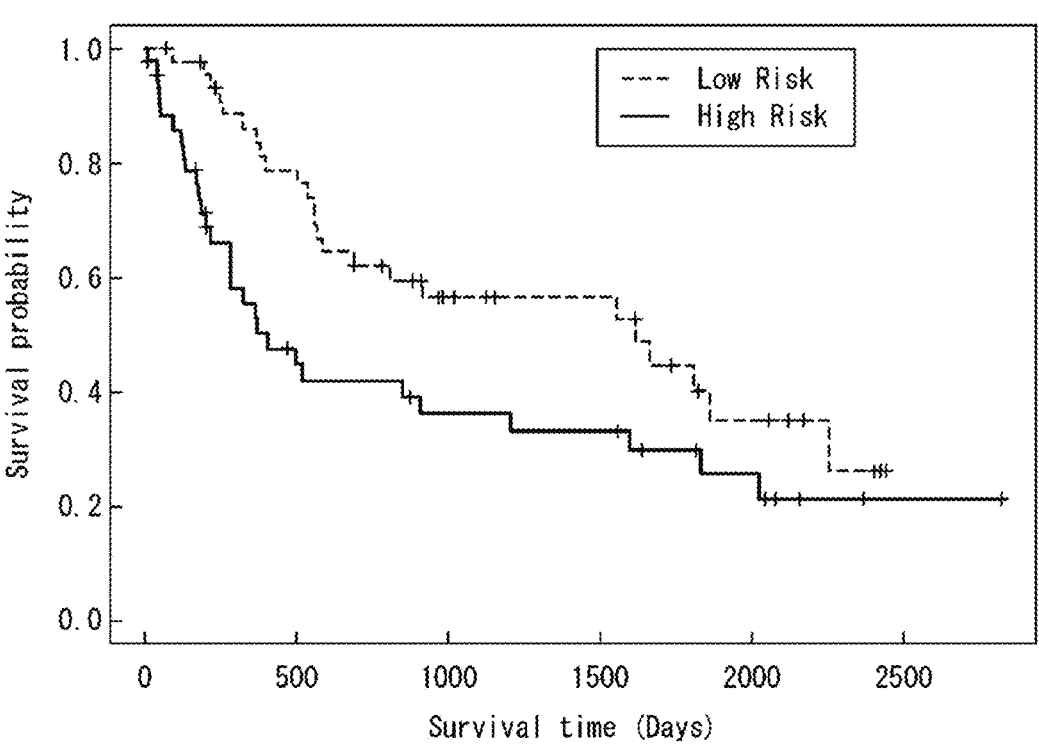
FIG. 23 is an eleventh diagram showing an experiment according to the embodiment.
Figure 24:
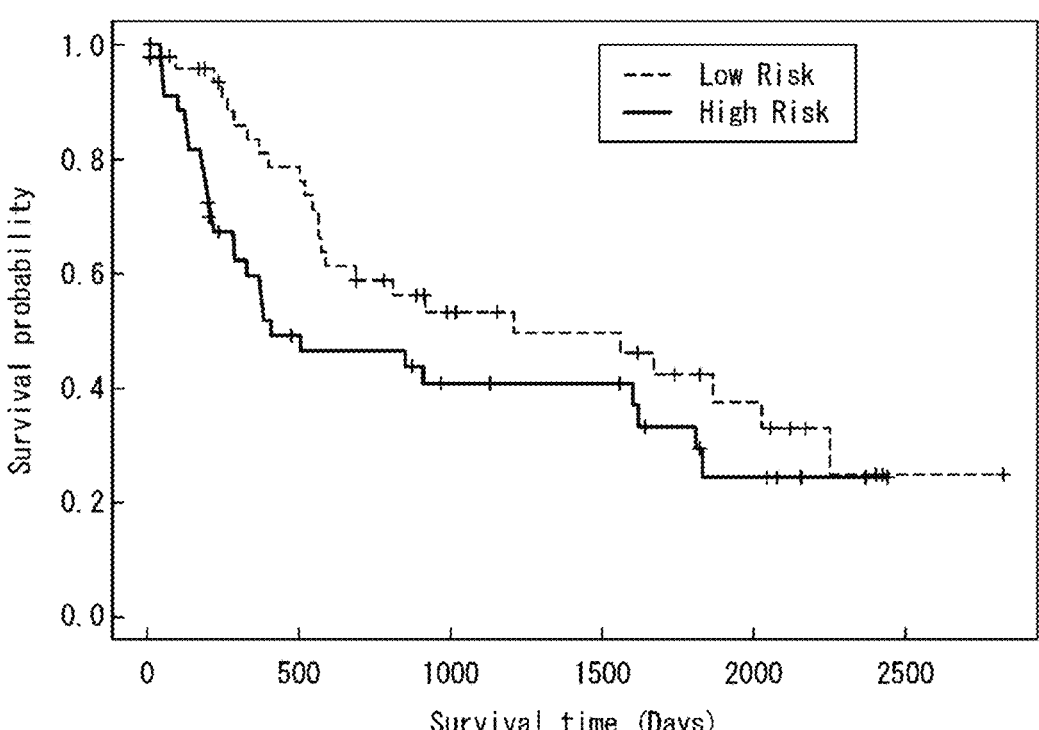
FIG. 24 is a twelfth diagram showing an experiment according to the embodiment.

With reference to FIGS. 23 and 24, effects of the prognosis prediction system 100 related to an evaluation using Kaplan-Meier curves will be described. In an experiment, test data was input to the prognosis prediction device 2 in advance, and thus a rad score was obtained for each test data. A median value of a distribution of rad scores obtained in the experiment was used as a boundary, and the test data was classified into test data with a rad score lower than the median value (hereinafter referred to as "low score data") and test data with a rad score equal to or larger than the median value (hereinafter referred to as "high score data").

In the experiment, whether there is a significant difference in a survival period between a set of pieces of low score data and a set of pieces of high score data was evaluated using the Kaplan-Meier curve. In the experiment, an evaluation of presence or absence of a significant difference in the survival period using the Kaplan-Meier curve was executed for each of the rad score obtained by the prognosis prediction system 100 and the rad score obtained by the technique in the related art.

FIG. 23 is an eleventh diagram showing an experiment according to the embodiment. More specifically, FIG. 23 is a diagram showing a result of an evaluation of presence or absence of a significant difference in a survival period using Kaplan-Meier curves for the rad score obtained by the prognosis prediction system 100. A horizontal axis in FIG. 23 indicates a survival period. A vertical axis in FIG. 23 indicates a survival probability. A line of "Low Risk" in FIG. 23 indicates a survival curve of a set of pieces of low score data. A line of "High Risk" in FIG. 23 indicates a survival curve of a set of pieces of high score data. As for the result of FIG. 23, a p value in the Kaplan-Meier curve was 0.004.

FIG. 24 is a twelfth diagram showing an experiment according to the embodiment. More specifically, FIG. 24 is a diagram showing a result of an evaluation of presence or absence of a significant difference in a survival period using Kaplan-Meier curves for the rad score obtained by the technique in the related art. A horizontal axis in FIG. 24 indicates a survival period. A vertical axis in FIG. 24 indicates a survival probability. A line of "Low Risk" in FIG. 24 indicates a survival curve of a set of pieces of low score data. A line of "High Risk" in FIG. 24 indicates a survival curve of a set of pieces of high score data. As for the result of FIG. 24, a p value in the Kaplan-Meier curve was 0.03.

FIGS. 23 and 24 show that the prognosis prediction system 100 can indicate a significant difference in the survival period using the Kaplan-Meier curve as in the technique in the related art.

In the experiment, accuracy of prognosis prediction was evaluated using a C-index. The C-index is an index of the accuracy of prognosis prediction, and the closer to 1, the higher the prediction accuracy, and the closer to 0.5, the lower the prediction accuracy.

In the experiment, the C-index was calculated using the test data. In the experiment, regarding the prediction accuracy by the prognosis prediction system 100, a value of a C-index was 0.679, and a p value in a Log-rank test was 0.004. In the experiment, regarding prediction accuracy by the technique in the related art, a value of a C-index was 0.625, and a p value in a Log-rank test was 0.01. Thus, in the experiment, the prediction accuracy by the prognosis prediction system 100 is higher than the prediction accuracy by the technique in the related art.

The prognosis prediction information acquisition device 1 of the embodiment configured thus acquires prognosis prediction information, which is information indicating a relationship between graph tumor information and a prognosis, using the graph tumor information. Therefore, the prognosis prediction information acquisition device 1 can improve accuracy of prognosis prediction for a patient having tumor disease.

The prognosis prediction device 2 of the embodiment configured thus predicts a prognosis using the prognosis prediction information, which is the information indicating the relationship between the graph tumor information and the prognosis, using the graph tumor information. Therefore, the prognosis prediction device 2 can improve the accuracy of the prognosis prediction for a patient having tumor disease.

The prognosis prediction system 100 of the embodiment configured thus acquires the prognosis prediction information, which is the information indicating the relationship between the graph tumor information and the prognosis, using the graph tumor information. Therefore, the prognosis prediction system 100 can improve the accuracy of the prognosis prediction for a patient having tumor disease. The prognosis prediction system 100 predicts a prognosis using the prognosis prediction information, which is the information indicating the relationship between the graph tumor information and the prognosis, using the graph tumor information. Therefore, the prognosis prediction system 100 can improve the accuracy of the prognosis prediction for a patient having tumor disease.

(Modification)

The graph amount may be, for example, a graph amount obtained from a graph in which a graph amount obtained for each region in a result of dividing a tumor image into a plurality of regions is used as a weight of a vertex.

Figure 25:
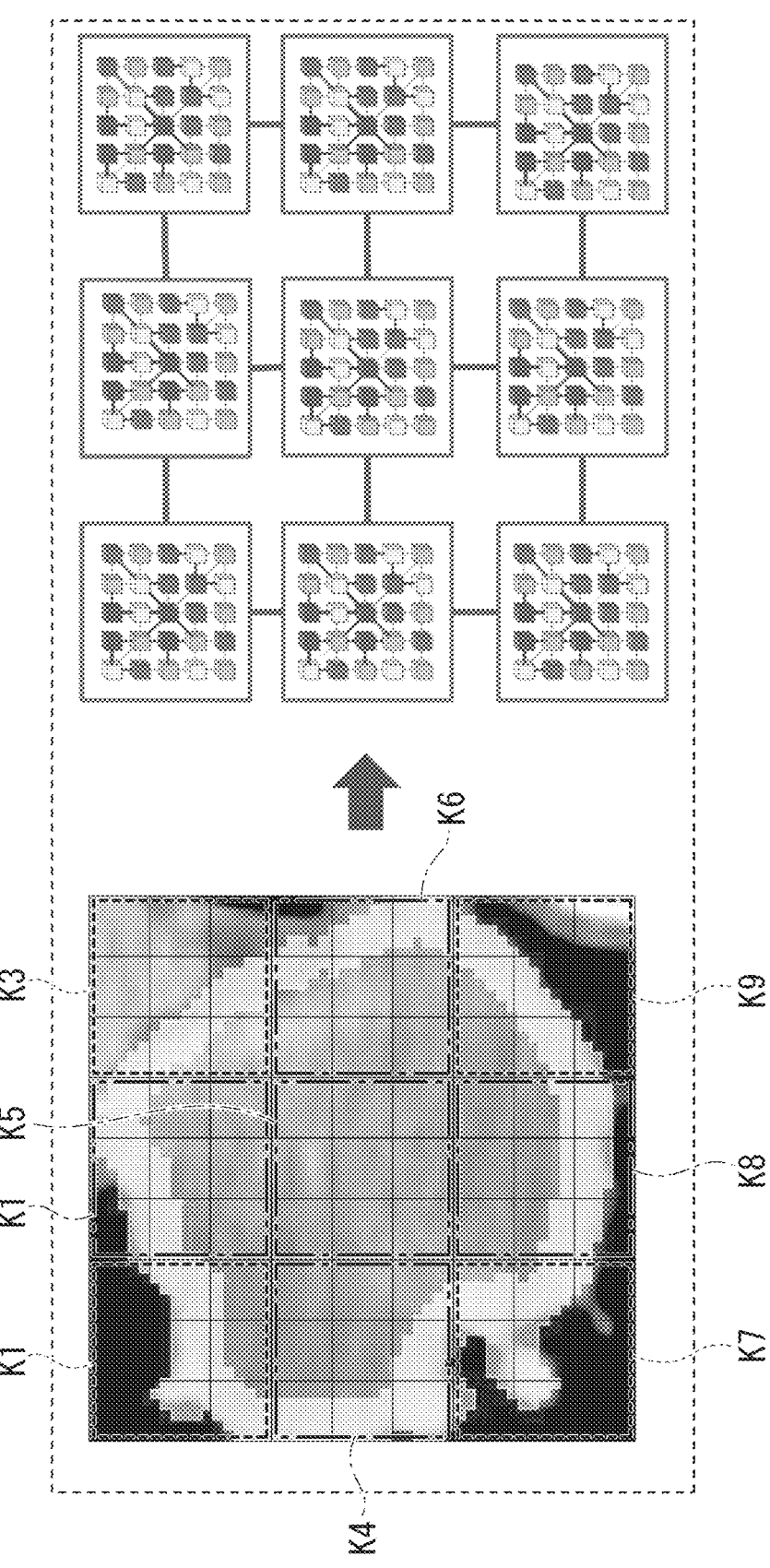
FIG. 25 is a diagram showing an example of a graph amount according to a modification.

FIG. 25 is a diagram showing an example of a graph amount in a modification. FIG. 25 shows that the tumor image is divided into nine regions K1 to K9. FIG. 25 shows that a graph is generated for each of the regions K1 to K9, and a graph having vertices with a graph amount obtained from a generated graph as a weight is generated.

The graph amount used by the prognosis prediction system 100 may be only the 1st graph feature. In such a case, according to an experiment using the test data of the 91 cases above, a C-index of the prognosis prediction system 100 was 0.657. According to the experiment using the test data of the 91 cases above, a p value in the Log-rank test of the prognosis prediction system 100 was 0.085, and a p value in the Kaplan-Meier curve of the prognosis prediction system 100 was 0.05.

The graph amount used by the prognosis prediction system 100 may be only the 5th graph feature. In such a case, according to an experiment using the test data of the 91 cases above, the C-index of the prognosis prediction system 100 was 0.632. According to the experiment using the test data of the 91 cases above, a p value in the Log-rank test of the prognosis prediction system 100 was 0.644, and a p value in the Kaplan-Meier curve of the prognosis prediction system 100 was 0.01.

The graph amount used by the prognosis prediction system 100 may be only the 2nd graph feature. In such a case, when a value of the edge threshold value is 5 HU, according to an experiment using the test data of the 91 cases above, the C-index of the prognosis prediction system 100 was 0.557. In such a case, when the value of the edge threshold value is 5 HU, according to the experiment using the test data of the 91 cases above, a p value in the Log-rank test of the prognosis prediction system 100 was 0.030, and a p value in the Kaplan-Meier curve of the prognosis prediction system 100 was 0.328.

The graph amount used by the prognosis prediction system 100 may be only the 7th graph feature. In such a case, when a value of the edge threshold value is 5 HU, according to an experiment using the test data of the 91 cases above, the C-index of the prognosis prediction system 100 was 0.546. In such a case, when the value of the edge threshold value is 5 HU, according to the experiment using the test data of the 91 cases above, a p value in the Log-rank test of the prognosis prediction system 100 was 0.046, and a p value in the Kaplan-Meier curve of the prognosis prediction system 100 was 0.135.

The graph amount used by the prognosis prediction system 100 may be only the 6th graph feature. In such a case, when a value of the edge threshold value is 5 HU, according to an experiment using the test data of the 91 cases above, the C-index of the prognosis prediction system 100 was 0.685. In such a case, when the value of the edge threshold value is 5 HU, according to the experiment using the test data of the 91 cases above, a p value in the Log-rank test of the prognosis prediction system 100 was 0.000, and a p value in the Kaplan-Meier curve of the prognosis prediction system 100 was 0.010.

The graph amount used by the prognosis prediction system 100 may be only the 4th graph feature. In such a case, when a value of the edge threshold value is 5 HU, according to an experiment using the test data of the 91 cases above, the C-index of the prognosis prediction system 100 was 0.641. In such a case, when the value of the edge threshold value is 5 HU, according to the experiment using the test data of the 91 cases above, a p value in the Log-rank test of the prognosis prediction system 100 was 0.118, and a p value in the Kaplan-Meier curve of the prognosis prediction system 100 was 0.044.

The graph amount used by the prognosis prediction system 100 may be only the 3rd graph feature. In such a case, when a value of the edge threshold value is 5 HU, according to an experiment using the test data of the 91 cases above, the C-index of the prognosis prediction system 100 was 0.415. In such a case, when the value of the edge threshold value is 5 HU, according to the experiment using the test data of the 91 cases above, a p value in the Log-rank test of the prognosis prediction system 100 was 0.328, and a p value in the Kaplan-Meier curve of the prognosis prediction system 100 was 0.349.

When the graph amount used by the prognosis prediction system 100 is only the 2nd graph feature, a value of the edge threshold value may be 10 HU. In such a case, according to an experiment using the test data of the 91 cases above, the C-index of the prognosis prediction system 100 was 0.490. In such a case, according to the experiment using the test data of the 91 cases above, a p value in the Log-rank test of the prognosis prediction system 100 was 0.293, and a p value in the Kaplan-Meier curve of the prognosis prediction system 100 was 0.517.

When the graph amount used by the prognosis prediction system 100 is only the 7th graph feature, a value of the edge threshold value may be 10 HU. In such a case, according to an experiment using the test data of the 91 cases above, the C-index of the prognosis prediction system 100 was 0.479. In such a case, according to the experiment using the test data of the 91 cases above, a p value in the Log-rank test of the prognosis prediction system 100 was 0.390, and a p value in the Kaplan-Meier curve of the prognosis prediction system 100 was 0.875.

When the graph amount used by the prognosis prediction system 100 is only the 6th graph feature, a value of the edge threshold value may be 10 HU. In such a case, according to an experiment using the test data of the 91 cases above, the C-index of the prognosis prediction system 100 was 0.665. In such a case, according to the experiment using the test data of the 91 cases above, a p value in the Log-rank test of the prognosis prediction system 100 was 0.001, and a p value in the Kaplan-Meier curve of the prognosis prediction system 100 was 0.006.

When the graph amount used by the prognosis prediction system 100 is only the 4th graph feature, a value of the edge threshold value may be 10 HU. In such a case, according to an experiment using the test data of the 91 cases above, the C-index of the prognosis prediction system 100 was 0.636. In such a case, according to the experiment using the test data of the 91 cases above, a p value in the Log-rank test of the prognosis prediction system 100 was 0.118, and a p value in the Kaplan-Meier curve of the prognosis prediction system 100 was 0.108.

When the graph amount used by the prognosis prediction system 100 is only the 3rd graph feature, a value of the edge threshold value may be 10 HU. In such a case, according to an experiment using the test data of the 91 cases above, the C-index of the prognosis prediction system 100 was 0.403. In such a case, according to the experiment using the test data of the 91 cases above, a p value in the Log-rank test of the prognosis prediction system 100 was 0.447, and a p value in the Kaplan-Meier curve of the prognosis prediction system 100 was 0.180.

When the graph amount used by the prognosis prediction system 100 is only the 2nd graph feature, a value of the edge threshold value may be 15 HU. In such a case, according to an experiment using the test data of the 91 cases above, the C-index of the prognosis prediction system 100 was 0.431. In such a case, according to the experiment using the test data of the 91 cases above, a p value in the Log-rank test of the prognosis prediction system 100 was 0.896, and a p value in the Kaplan-Meier curve of the prognosis prediction system 100 was 0.780.

When the graph amount used by the prognosis prediction system 100 is only the 7th graph feature, a value of the edge threshold value may be 15 HU. In such a case, according to an experiment using the test data of the 91 cases above, the C-index of the prognosis prediction system 100 was 0.424. In such a case, according to the experiment using the test data of the 91 cases above, a p value in the Log-rank test of the prognosis prediction system 100 was 0.990, and a p value in the Kaplan-Meier curve of the prognosis prediction system 100 was 0.780.

When the graph amount used by the prognosis prediction system 100 is only the 6th graph feature, a value of the edge threshold value may be 15 HU. In such a case, according to an experiment using the test data of the 91 cases above, the C-index of the prognosis prediction system 100 was 0.589. In such a case, according to the experiment using the test data of the 91 cases above, a p value in the Log-rank test of the prognosis prediction system 100 was 0.021, and a p value in the Kaplan-Meier curve of the prognosis prediction system 100 was 0.459.

When the graph amount used by the prognosis prediction system 100 is only the 4th graph feature, a value of the edge threshold value may be 15 HU. In such a case, according to an experiment using the test data of the 91 cases above, the C-index of the prognosis prediction system 100 was 0.631. In such a case, according to the experiment using the test data of the 91 cases above, a p value in the Log-rank test of the prognosis prediction system 100 was 0.112, and a p value in the Kaplan-Meier curve of the prognosis prediction system 100 was 0.118.

When the graph amount used by the prognosis prediction system 100 is only the 3rd graph feature, a value of the edge threshold value may be 15 HU. In such a case, according to an experiment using the test data of the 91 cases above, the C-index of the prognosis prediction system 100 was 0.387. In such a case, according to the experiment using the test data of the 91 cases above, a p value in the Log-rank test of the prognosis prediction system 100 was 0.575, and a p value in the Kaplan-Meier curve of the prognosis prediction system 100 was 0.156.

When the graph amount used by the prognosis prediction system 100 is only the 2nd graph feature, a value of the edge threshold value may be 20 HU. In such a case, according to an experiment using the test data of the 91 cases above, the C-index of the prognosis prediction system 100 was 0.606. In such a case, according to the experiment using the test data of the 91 cases above, a p value in the Log-rank test of the prognosis prediction system 100 was 0.687, and a p value in the Kaplan-Meier curve of the prognosis prediction system 100 was 0.243.

When the graph amount used by the prognosis prediction system 100 is only the 7th graph feature, a value of the edge threshold value may be 20 HU. In such a case, according to an experiment using the test data of the 91 cases above, the C-index of the prognosis prediction system 100 was 0.612. In such a case, according to the experiment using the test data of the 91 cases above, a p value in the Log-rank test of the prognosis prediction system 100 was 0.643, and a p value in the Kaplan-Meier curve of the prognosis prediction system 100 was 0.078.

When the graph amount used by the prognosis prediction system 100 is only the 6th graph feature, a value of the edge threshold value may be 20 HU. In such a case, according to an experiment using the test data of the 91 cases above, the C-index of the prognosis prediction system 100 was 0.524. In such a case, according to the experiment using the test data of the 91 cases above, a p value in the Log-rank test of the prognosis prediction system 100 was 0.187, and a p value in the Kaplan-Meier curve of the prognosis prediction system 100 was 0.799.

When the graph amount used by the prognosis prediction system 100 is only the 4th graph feature, a value of the edge threshold value may be 20 HU. In such a case, according to an experiment using the test data of the 91 cases above, the C-index of the prognosis prediction system 100 was 0.631. In such a case, according to the experiment using the test data of the 91 cases above, a p value in the Log-rank test of the prognosis prediction system 100 was 0.115, and a p value in the Kaplan-Meier curve of the prognosis prediction system 100 was 0.118.

When the graph amount used by the prognosis prediction system 100 is only the 3rd graph feature, a value of the edge threshold value may be 20 HU. In such a case, according to an experiment using the test data of the 91 cases above, the C-index of the prognosis prediction system 100 was 0.375. In such a case, according to the experiment using the test data of the 91 cases above, a p value in the Log-rank test of the prognosis prediction system 100 was 0.660, and a p value in the Kaplan-Meier curve of the prognosis prediction system 100 was 0.156.

When the graph amount used by the prognosis prediction system 100 is only the 2nd graph feature, a value of the edge threshold value may be 25 HU. In such a case, according to an experiment using the test data of the 91 cases above, the C-index of the prognosis prediction system 100 was 0.629. In such a case, according to the experiment using the test data of the 91 cases above, a p value in the Log-rank test of the prognosis prediction system 100 was 0.498, and a p value in the Kaplan-Meier curve of the prognosis prediction system 100 was 0.016.

When the graph amount used by the prognosis prediction system 100 is only the 7th graph feature, a value of the edge threshold value may be 25 HU. In such a case, according to an experiment using the test data of the 91 cases above, the C-index of the prognosis prediction system 100 was 0.633. In such a case, according to the experiment using the test data of the 91 cases above, a p value in the Log-rank test of the prognosis prediction system 100 was 0.486, and a p value in the Kaplan-Meier curve of the prognosis prediction system 100 was 0.007.

When the graph amount used by the prognosis prediction system 100 is only the 6th graph feature, a value of the edge threshold value may be 25 HU. In such a case, according to an experiment using the test data of the 91 cases above, the C-index of the prognosis prediction system 100 was 0.464. In such a case, according to the experiment using the test data of the 91 cases above, a p value in the Log-rank test of the prognosis prediction system 100 was 0.933, and a p value in the Kaplan-Meier curve of the prognosis prediction system 100 was 0.854.

When the graph amount used by the prognosis prediction system 100 is only the 4th graph feature, a value of the edge threshold value may be 25 HU. In such a case, according to an experiment using the test data of the 91 cases above, the C-index of the prognosis prediction system 100 was 0.629. In such a case, according to the experiment using the test data of the 91 cases above, a p value in the Log-rank test of the prognosis prediction system 100 was 0.117, and a p value in the Kaplan-Meier curve of the prognosis prediction system 100 was 0.118.

When the graph amount used by the prognosis prediction system 100 is only the 3rd graph feature, a value of the edge threshold value may be 25 HU. In such a case, according to an experiment using the test data of the 91 cases above, the C-index of the prognosis prediction system 100 was 0.369. In such a case, according to the experiment using the test data of the 91 cases above, a p value in the Log-rank test of the prognosis prediction system 100 was 0.700, and a p value in the Kaplan-Meier curve of the prognosis prediction system 100 was 0.063.

When the graph amount used by the prognosis prediction system 100 is only the 2nd graph feature, a value of the edge threshold value may be 30 HU. In such a case, according to an experiment using the test data of the 91 cases above, the C-index of the prognosis prediction system 100 was 0.641. In such a case, according to the experiment using the test data of the 91 cases above, a p value in the Log-rank test of the prognosis prediction system 100 was 0.445, and a p value in the Kaplan-Meier curve of the prognosis prediction system 100 was 0.005.

When the graph amount used by the prognosis prediction system 100 is only the 7th graph feature, a value of the edge threshold value may be 30 HU. In such a case, according to an experiment using the test data of the 91 cases above, the C-index of the prognosis prediction system 100 was 0.640. In such a case, according to the experiment using the test data of the 91 cases above, a p value in the Log-rank test of the prognosis prediction system 100 was 0.467, and a p value in the Kaplan-Meier curve of the prognosis prediction system 100 was 0.005.

When the graph amount used by the prognosis prediction system 100 is only the 6th graph feature, a value of the edge threshold value may be 30 HU. In such a case, according to an experiment using the test data of the 91 cases above, the C-index of the prognosis prediction system 100 was 0.611. In such a case, according to the experiment using the test data of the 91 cases above, a p value in the Log-rank test of the prognosis prediction system 100 was 0.139, and a p value in the Kaplan-Meier curve of the prognosis prediction system 100 was 0.117.

When the graph amount used by the prognosis prediction system 100 is only the 4th graph feature, a value of the edge threshold value may be 30 HU. In such a case, according to an experiment using the test data of the 91 cases above, the C-index of the prognosis prediction system 100 was 0.629. In such a case, according to the experiment using the test data of the 91 cases above, a p value in the Log-rank test of the prognosis prediction system 100 was 0.122, and a p value in the Kaplan-Meier curve of the prognosis prediction system 100 was 0.118.

When the graph amount used by the prognosis prediction system 100 is only the 3rd graph feature, a value of the edge threshold value may be 30 HU. In such a case, according to an experiment using the test data of the 91 cases above, the C-index of the prognosis prediction system 100 was 0.363. In such a case, according to the experiment using the test data of the 91 cases above, a p value in the Log-rank test of the prognosis prediction system 100 was 0.696, and a p value in the Kaplan-Meier curve of the prognosis prediction system 100 was 0.021.

When the graph amount used by the prognosis prediction system 100 is only the 2nd graph feature, a value of the edge threshold value may be 35 HU. In such a case, according to an experiment using the test data of the 91 cases above, the C-index of the prognosis prediction system 100 was 0.644. In such a case, according to the experiment using the test data of the 91 cases above, a p value in the Log-rank test of the prognosis prediction system 100 was 0.480, and a p value in the Kaplan-Meier curve of the prognosis prediction system 100 was 0.005.

When the graph amount used by the prognosis prediction system 100 is only the 7th graph feature, a value of the edge threshold value may be 35 HU. In such a case, according to an experiment using the test data of the 91 cases above, the C-index of the prognosis prediction system 100 was 0.647. In such a case, according to the experiment using the test data of the 91 cases above, a p value in the Log-rank test of the prognosis prediction system 100 was 0.484, and a p value in the Kaplan-Meier curve of the prognosis prediction system 100 was 0.005.

When the graph amount used by the prognosis prediction system 100 is only the 6th graph feature, a value of the edge threshold value may be 35 HU. In such a case, according to an experiment using the test data of the 91 cases above, the C-index of the prognosis prediction system 100 was 0.606. In such a case, according to the experiment using the test data of the 91 cases above, a p value in the Log-rank test of the prognosis prediction system 100 was 0.460, and a p value in the Kaplan-Meier curve of the prognosis prediction system 100 was 0.317.

When the graph amount used by the prognosis prediction system 100 is only the 4th graph feature, a value of the edge threshold value may be 35 HU. In such a case, according to an experiment using the test data of the 91 cases above, the C-index of the prognosis prediction system 100 was 0.627. In such a case, according to the experiment using the test data of the 91 cases above, a p value in the Log-rank test of the prognosis prediction system 100 was 0.153, and a p value in the Kaplan-Meier curve of the prognosis prediction system 100 was 0.118.

When the graph amount used by the prognosis prediction system 100 is only the 3rd graph feature, a value of the edge threshold value may be 35 HU. In such a case, according to an experiment using the test data of the 91 cases above, the C-index of the prognosis prediction system 100 was 0.364. In such a case, according to the experiment using the test data of the 91 cases above, a p value in the Log-rank test of the prognosis prediction system 100 was 0.651, and a p value in the Kaplan-Meier curve of the prognosis prediction system 100 was 0.021.

When the graph amount used by the prognosis prediction system 100 is only the 2nd graph feature, a value of the edge threshold value may be 40 HU. In such a case, according to an experiment using the test data of the 91 cases above, the C-index of the prognosis prediction system 100 was 0.645. In such a case, according to the experiment using the test data of the 91 cases above, a p value in the Log-rank test of the prognosis prediction system 100 was 0.530, and a p value in the Kaplan-Meier curve of the prognosis prediction system 100 was 0.005.

When the graph amount used by the prognosis prediction system 100 is only the 7th graph feature, a value of the edge threshold value may be 40 HU. In such a case, according to an experiment using the test data of the 91 cases above, the C-index of the prognosis prediction system 100 was 0.646. In such a case, according to the experiment using the test data of the 91 cases above, a p value in the Log-rank test of the prognosis prediction system 100 was 0.553, and a p value in the Kaplan-Meier curve of the prognosis prediction system 100 was 0.005.

When the graph amount used by the prognosis prediction system 100 is only the 6th graph feature, a value of the edge threshold value may be 40 HU. In such a case, according to an experiment using the test data of the 91 cases above, the C-index of the prognosis prediction system 100 was 0.643. In such a case, according to the experiment using the test data of the 91 cases above, a p value in the Log-rank test of the prognosis prediction system 100 was 0.128, and a p value in the Kaplan-Meier curve of the prognosis prediction system 100 was 0.031.

When the graph amount used by the prognosis prediction system 100 is only the 4th graph feature, a value of the edge threshold value may be 40 HU. In such a case, according to an experiment using the test data of the 91 cases above, the C-index of the prognosis prediction system 100 was 0.628. In such a case, according to the experiment using the test data of the 91 cases above, a p value in the Log-rank test of the prognosis prediction system 100 was 0.157, and a p value in the Kaplan-Meier curve of the prognosis prediction system 100 was 0.118.

When the graph amount used by the prognosis prediction system 100 is only the 3rd graph feature, a value of the edge threshold value may be 40 HU. In such a case, according to an experiment using the test data of the 91 cases above, the C-index of the prognosis prediction system 100 was 0.363. In such a case, according to the experiment using the test data of the 91 cases above, a p value in the Log-rank test of the prognosis prediction system 100 was 0.598, and a p value in the Kaplan-Meier curve of the prognosis prediction system 100 was 0.022.

When the graph amount used by the prognosis prediction system 100 is only the 2nd graph feature, a value of the edge threshold value may be 45 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.625, and a p value in the Kaplan-Meier curve of the prognosis prediction system 100 was 0.005.

When the graph amount used by the prognosis prediction system 100 is only the 7th graph feature, a value of the edge threshold value may be 45 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.661, and a p value in the Kaplan-Meier curve of the prognosis prediction system 100 was 0.015.

When the graph amount used by the prognosis prediction system 100 is only the 6th graph feature, a value of the edge threshold value may be 45 HU. In such a case, according to an experiment using the test data of the 91 cases above, the C-index of the prognosis prediction system 100 was 0.663. In such a case, according to the experiment using the test data of the 91 cases above, a p value in the Log-rank test of the prognosis prediction system 100 was 0.054, and a p value in the Kaplan-Meier curve of the prognosis prediction system 100 was 0.029.

When the graph amount used by the prognosis prediction system 100 is only the 4th graph feature, a value of the edge threshold value may be 45 HU. In such a case, according to an experiment using the test data of the 91 cases above, the C-index of the prognosis prediction system 100 was 0.628. In such a case, according to the experiment using the test data of the 91 cases above, a p value in the Log-rank test of the prognosis prediction system 100 was 0.166, and a p value in the Kaplan-Meier curve of the prognosis prediction system 100 was 0.048.

When the graph amount used by the prognosis prediction system 100 is only the 3rd graph feature, a value of the edge threshold value may be 45 HU. In such a case, according to an experiment using the test data of the 91 cases above, the C-index of the prognosis prediction system 100 was 0.365. In such a case, according to the experiment using the test data of the 91 cases above, a p value in the Log-rank test of the prognosis prediction system 100 was 0.527, and a p value in the Kaplan-Meier curve of the prognosis prediction system 100 was 0.038.

When the graph amount used by the prognosis prediction system 100 is only the 2nd graph feature, a value of the edge threshold value may be 50 HU. In such a case, according to an experiment using the test data of the 91 cases above, the C-index of the prognosis prediction system 100 was 0.643. In such a case, according to the experiment using the test data of the 91 cases above, a p value in the Log-rank test of the prognosis prediction system 100 was 0.756, and a p value in the Kaplan-Meier curve of the prognosis prediction system 100 was 0.012.

When the graph amount used by the prognosis prediction system 100 is only the 7th graph feature, a value of the edge threshold value may be 50 HU. In such a case, according to an experiment using the test data of the 91 cases above, the C-index of the prognosis prediction system 100 was 0.641. In such a case, according to the experiment using the test data of the 91 cases above, a p value in the Log-rank test of the prognosis prediction system 100 was 0.784, and a p value in the Kaplan-Meier curve of the prognosis prediction system 100 was 0.012.

When the graph amount used by the prognosis prediction system 100 is only the 6th graph feature, a value of the edge threshold value may be 50 HU. In such a case, according to an experiment using the test data of the 91 cases above, the C-index of the prognosis prediction system 100 was 0.667. In such a case, according to the experiment using the test data of the 91 cases above, a p value in the Log-rank test of the prognosis prediction system 100 was 0.051, and a p value in the Kaplan-Meier curve of the prognosis prediction system 100 was 0.007.

When the graph amount used by the prognosis prediction system 100 is only the 4th graph feature, a value of the edge threshold value may be 50 HU. In such a case, according to an experiment using the test data of the 91 cases above, the C-index of the prognosis prediction system 100 was 0.626. In such a case, according to the experiment using the test data of the 91 cases above, a p value in the Log-rank test of the prognosis prediction system 100 was 0.177, and a p value in the Kaplan-Meier curve of the prognosis prediction system 100 was 0.048.

When the graph amount used by the prognosis prediction system 100 is only the 3rd graph feature, a value of the edge threshold value may be 50 HU. In such a case, according to an experiment using the test data of the 91 cases above, the C-index of the prognosis prediction system 100 was 0.369. In such a case, according to the experiment using the test data of the 91 cases above, a p value in the Log-rank test of the prognosis prediction system 100 was 0.450, and a p value in the Kaplan-Meier curve of the prognosis prediction system 100 was 0.038.

The graph amount used by the prognosis prediction system 100 may be only the 9th graph feature. In such a case, when a value of the edge threshold value is 5 HU, according to an experiment using the test data of the 91 cases above, the C-index of the prognosis prediction system 100 was 0.632. In such a case, when the value of the edge threshold value is 5 HU, according to the experiment using the test data of the 91 cases above, a p value in the Log-rank test of the prognosis prediction system 100 was 0.047, and a p value in the Kaplan-Meier curve of the prognosis prediction system 100 was 0.077.

The graph amount used by the prognosis prediction system 100 may be only the 8th graph feature. In such a case, when a value of the edge threshold value is 5 HU, according to an experiment using the test data of the 91 cases above, the C-index of the prognosis prediction system 100 was 0.557. In such a case, when the value of the edge threshold value is 5 HU, according to the experiment using the test data of the 91 cases above, a p value in the Log-rank test of the prognosis prediction system 100 was 0.030, and a p value in the Kaplan-Meier curve of the prognosis prediction system 100 was 0.328.

When the graph amount used by the prognosis prediction system 100 is only the 9th graph feature, a value of the edge threshold value may be 10 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.041, and a p value in the Kaplan-Meier curve of the prognosis prediction system 100 was 0.040.

When the graph amount used by the prognosis prediction system 100 is only the 8th graph feature, the edge threshold value may be 10 HU. In such a case, according to an experiment using the test data of the 91 cases above, the C-index of the prognosis prediction system 100 was 0.490. In such a case, according to the experiment using the test data of the 91 cases above, a p value in the Log-rank test of the prognosis prediction system 100 was 0.293, and a p value in the Kaplan-Meier curve of the prognosis prediction system 100 was 0.517.

When the graph amount used by the prognosis prediction system 100 is only the 9th graph feature, a value of the edge threshold value may be 15 HU. In such a case, according to an experiment using the test data of the 91 cases above, the C-index of the prognosis prediction system 100 was 0.652. In such a case, according to the experiment using the test data of the 91 cases above, a p value in the Log-rank test of the prognosis prediction system 100 was 0.039, and a p value in the Kaplan-Meier curve of the prognosis prediction system 100 was 0.031.

When the graph amount used by the prognosis prediction system 100 is only the 8th graph feature, a value of the edge threshold value may be 15 HU. In such a case, according to an experiment using the test data of the 91 cases above, the C-index of the prognosis prediction system 100 was 0.431. In such a case, according to the experiment using the test data of the 91 cases above, a p value in the Log-rank test of the prognosis prediction system 100 was 0.896, and a p value in the Kaplan-Meier curve of the prognosis prediction system 100 was 0.780.

When the graph amount used by the prognosis prediction system 100 is only the 9th graph feature, a value of the edge threshold value may be 20 HU. In such a case, according to an experiment using the test data of the 91 cases above, the C-index of the prognosis prediction system 100 was 0.659. In such a case, according to the experiment using the test data of the 91 cases above, a p value in the Log-rank test of the prognosis prediction system 100 was 0.039, and a p value in the Kaplan-Meier curve of the prognosis prediction system 100 was 0.058.

When the graph amount used by the prognosis prediction system 100 is only the 8th graph feature, a value of the edge threshold value may be 20 HU. In such a case, according to an experiment using the test data of the 91 cases above, the C-index of the prognosis prediction system 100 was 0.606. In such a case, according to the experiment using the test data of the 91 cases above, a p value in the Log-rank test of the prognosis prediction system 100 was 0.687, and a p value in the Kaplan-Meier curve of the prognosis prediction system 100 was 0.243.

When the graph amount used by the prognosis prediction system 100 is only the 9th graph feature, a value of the edge threshold value may be 25 HU. In such a case, according to an experiment using the test data of the 91 cases above, the C-index of the prognosis prediction system 100 was 0.663. In such a case, according to the experiment using the test data of the 91 cases above, a p value in the Log-rank test of the prognosis prediction system 100 was 0.040, and a p value in the Kaplan-Meier curve of the prognosis prediction system 100 was 0.047.

When the graph amount used by the prognosis prediction system 100 is only the 8th graph feature, a value of the edge threshold value may be 25 HU. In such a case, according to an experiment using the test data of the 91 cases above, the C-index of the prognosis prediction system 100 was 0.629. In such a case, according to the experiment using the test data of the 91 cases above, a p value in the Log-rank test of the prognosis prediction system 100 was 0.498, and a p value in the Kaplan-Meier curve of the prognosis prediction system 100 was 0.016.

When the graph amount used by the prognosis prediction system 100 is only the 9th graph feature, a value of the edge threshold value may be 30 HU. In such a case, according to an experiment using the test data of the 91 cases above, the C-index of the prognosis prediction system 100 was 0.671. In such a case, according to the experiment using the test data of the 91 cases above, a p value in the Log-rank test of the prognosis prediction system 100 was 0.042, and a p value in the Kaplan-Meier curve of the prognosis prediction system 100 was 0.049.

When the graph amount used by the prognosis prediction system 100 is only the 8th graph feature, a value of the edge threshold value may be 30 HU. In such a case, according to an experiment using the test data of the 91 cases above, the C-index of the prognosis prediction system 100 was 0.641. In such a case, according to the experiment using the test data of the 91 cases above, a p value in the Log-rank test of the prognosis prediction system 100 was 0.445, and a p value in the Kaplan-Meier curve of the prognosis prediction system 100 was 0.005.

When the graph amount used by the prognosis prediction system 100 is only the 9th graph feature, a value of the edge threshold value may be 35 HU. In such a case, according to an experiment using the test data of the 91 cases above, the C-index of the prognosis prediction system 100 was 0.675. In such a case, according to the experiment using the test data of the 91 cases above, a p value in the Log-rank test of the prognosis prediction system 100 was 0.046, and a p value in the Kaplan-Meier curve of the prognosis prediction system 100 was 0.049.

When the graph amount used by the prognosis prediction system 100 is only the 8th graph feature, a value of the edge threshold value may be 35 HU. In such a case, according to an experiment using the test data of the 91 cases above, the C-index of the prognosis prediction system 100 was 0.644. In such a case, according to the experiment using the test data of the 91 cases above, a p value in the Log-rank test of the prognosis prediction system 100 was 0.480, and a p value in the Kaplan-Meier curve of the prognosis prediction system 100 was 0.005.

When the graph amount used by the prognosis prediction system 100 is only the 9th graph feature, a value of the edge threshold value may be 40 HU. In such a case, according to an experiment using the test data of the 91 cases above, the C-index of the prognosis prediction system 100 was 0.674. In such a case, according to the experiment using the test data of the 91 cases above, a p value in the Log-rank test of the prognosis prediction system 100 was 0.050, and a p value in the Kaplan-Meier curve of the prognosis prediction system 100 was 0.049.

When the graph amount used by the prognosis prediction system 100 is only the 8th graph feature, a value of the edge threshold value may be 40 HU. In such a case, according to an experiment using the test data of the 91 cases above, the C-index of the prognosis prediction system 100 was 0.645. In such a case, according to the experiment using the test data of the 91 cases above, a p value in the Log-rank test of the prognosis prediction system 100 was 0.530, and a p value in the Kaplan-Meier curve of the prognosis prediction system 100 was 0.005.

When the graph amount used by the prognosis prediction system 100 is only the 9th graph feature, a value of the edge threshold value may be 45 HU. In such a case, according to an experiment using the test data of the 91 cases above, the C-index of the prognosis prediction system 100 was 0.673. In such a case, according to the experiment using the test data of the 91 cases above, a p value in the Log-rank test of the prognosis prediction system 100 was 0.059, and a p value in the Kaplan-Meier curve of the prognosis prediction system 100 was 0.049.

When the graph amount used by the prognosis prediction system 100 is only the 8th graph feature, a value of the edge threshold value may be 45 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.625, and a p value in the Kaplan-Meier curve of the prognosis prediction system 100 was 0.005.

When the graph amount used by the prognosis prediction system 100 is only the 9th graph feature, a value of the edge threshold value may be 50 HU. In such a case, according to an experiment using the test data of the 91 cases above, the C-index of the prognosis prediction system 100 was 0.671. In such a case, according to the experiment using the test data of the 91 cases above, a p value in the Log-rank test of the prognosis prediction system 100 was 0.072, and a p value in the Kaplan-Meier curve of the prognosis prediction system 100 was 0.049.

When the graph amount used by the prognosis prediction system 100 is only the 8th graph feature, a value of the edge threshold value may be 50 HU. In such a case, according to an experiment using the test data of the 91 cases above, the C-index of the prognosis prediction system 100 was 0.643. In such a case, according to the experiment using the test data of the 91 cases above, a p value in the Log-rank test of the prognosis prediction system 100 was 0.756, and a p value in the Kaplan-Meier curve of the prognosis prediction system 100 was 0.012.

The graph amount used by the prognosis prediction system 100 may be only the 10th graph feature. In such a case, when a value of the edge threshold value is 5 HU, according to an experiment using the test data of the 91 cases above, the C-index of the prognosis prediction system 100 was 0.408. In such a case, when the value of the edge threshold value is 5 HU, according to the experiment using the test data of the 91 cases above, a p value in the Log-rank test of the prognosis prediction system 100 was 0.551, and a p value in the Kaplan-Meier curve of the prognosis prediction system 100 was 0.244.

The graph amount used by the prognosis prediction system 100 may be only the 12th graph feature. In such a case, when a value of the edge threshold value is 5 HU, according to an experiment using the test data of the 91 cases above, the C-index of the prognosis prediction system 100 was 0.644. In such a case, when the value of the edge threshold value is 5 HU, according to the experiment using the test data of the 91 cases above, a p value in the Log-rank test of the prognosis prediction system 100 was 0.249, and a p value in the Kaplan-Meier curve of the prognosis prediction system 100 was 0.024.

The graph amount used by the prognosis prediction system 100 may be only the 11th graph feature. In such a case, when a value of the edge threshold value is 5 HU, according to an experiment using the test data of the 91 cases above, the C-index of the prognosis prediction system 100 was 0.619. In such a case, when the value of the edge threshold value is 5 HU, according to the experiment using the test data of the 91 cases above, a p value in the Log-rank test of the prognosis prediction system 100 was 0.009, and a p value in the Kaplan-Meier curve of the prognosis prediction system 100 was 0.033.

When the graph amount used by the prognosis prediction system 100 is only the 10th graph feature, a value of the edge threshold value may be 10 HU. In such a case, according to an experiment using the test data of the 91 cases above, the C-index of the prognosis prediction system 100 was 0.446. In such a case, according to the experiment using the test data of the 91 cases above, a p value in the Log-rank test of the prognosis prediction system 100 was 0.320, and a p value in the Kaplan-Meier curve of the prognosis prediction system 100 was 0.710.

When the graph amount used by the prognosis prediction system 100 is only the 12th graph feature, a value of the edge threshold value may be 10 HU. In such a case, according to an experiment using the test data of the 91 cases above, the C-index of the prognosis prediction system 100 was 0.640. In such a case, according to the experiment using the test data of the 91 cases above, a p value in the Log-rank test of the prognosis prediction system 100 was 0.247, and a p value in the Kaplan-Meier curve of the prognosis prediction system 100 was 0.017.

When the graph amount used by the prognosis prediction system 100 is only the 11th graph feature, a value of the edge threshold value may be 10 HU. In such a case, according to an experiment using the test data of the 91 cases above, the C-index of the prognosis prediction system 100 was 0.560. In such a case, according to the experiment using the test data of the 91 cases above, a p value in the Log-rank test of the prognosis prediction system 100 was 0.037, and a p value in the Kaplan-Meier curve of the prognosis prediction system 100 was 0.430.

When the graph amount used by the prognosis prediction system 100 is only the 10th graph feature, a value of the edge threshold value may be 15 HU. In such a case, according to an experiment using the test data of the 91 cases above, the C-index of the prognosis prediction system 100 was 0.425. In such a case, according to the experiment using the test data of the 91 cases above, a p value in the Log-rank test of the prognosis prediction system 100 was 0.753, and a p value in the Kaplan-Meier curve of the prognosis prediction system 100 was 0.260.

When the graph amount used by the prognosis prediction system 100 is only the 12th graph feature, a value of the edge threshold value may be 15 HU. In such a case, according to an experiment using the test data of the 91 cases above, the C-index of the prognosis prediction system 100 was 0.640. In such a case, according to the experiment using the test data of the 91 cases above, a p value in the Log-rank test of the prognosis prediction system 100 was 0.207, and a p value in the Kaplan-Meier curve of the prognosis prediction system 100 was 0.009.

When the graph amount used by the prognosis prediction system 100 is only the 11th graph feature, a value of the edge threshold value may be 15 HU. In such a case, according to an experiment using the test data of the 91 cases above, the C-index of the prognosis prediction system 100 was 0.496. In such a case, according to the experiment using the test data of the 91 cases above, a p value in the Log-rank test of the prognosis prediction system 100 was 0.405, and a p value in the Kaplan-Meier curve of the prognosis prediction system 100 was 0.697.

When the graph amount used by the prognosis prediction system 100 is only the 10th graph feature, a value of the edge threshold value may be 20 HU. In such a case, according to an experiment using the test data of the 91 cases above, the C-index of the prognosis prediction system 100 was 0.611. In such a case, according to the experiment using the test data of the 91 cases above, a p value in the Log-rank test of the prognosis prediction system 100 was 0.682, and a p value in the Kaplan-Meier curve of the prognosis prediction system 100 was 0.188.

When the graph amount used by the prognosis prediction system 100 is only the 12th graph feature, a value of the edge threshold value may be 20 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.177, and a p value in the Kaplan-Meier curve of the prognosis prediction system 100 was 0.009.

When the graph amount used by the prognosis prediction system 100 is only the 11th graph feature, a value of the edge threshold value may be 20 HU. In such a case, according to an experiment using the test data of the 91 cases above, the C-index of the prognosis prediction system 100 was 0.577. In such a case, according to the experiment using the test data of the 91 cases above, a p value in the Log-rank test of the prognosis prediction system 100 was 0.749, and a p value in the Kaplan-Meier curve of the prognosis prediction system 100 was 0.369.

When the graph amount used by the prognosis prediction system 100 is only the 10th graph feature, a value of the edge threshold value may be 25 HU. In such a case, according to an experiment using the test data of the 91 cases above, the C-index of the prognosis prediction system 100 was 0.633. In such a case, according to the experiment using the test data of the 91 cases above, a p value in the Log-rank test of the prognosis prediction system 100 was 0.356, and a p value in the Kaplan-Meier curve of the prognosis prediction system 100 was 0.030.

When the graph amount used by the prognosis prediction system 100 is only the 12th graph feature, a value of the edge threshold value may be 25 HU. In such a case, according to an experiment using the test data of the 91 cases above, the C-index of the prognosis prediction system 100 was 0.640. In such a case, according to the experiment using the test data of the 91 cases above, a p value in the Log-rank test of the prognosis prediction system 100 was 0.170, and a p value in the Kaplan-Meier curve of the prognosis prediction system 100 was 0.009.

When the graph amount used by the prognosis prediction system 100 is only the 11th graph feature, a value of the edge threshold value may be 25 HU. In such a case, according to an experiment using the test data of the 91 cases above, the C-index of the prognosis prediction system 100 was 0.616. In such a case, according to the experiment using the test data of the 91 cases above, a p value in the Log-rank test of the prognosis prediction system 100 was 0.287, and a p value in the Kaplan-Meier curve of the prognosis prediction system 100 was 0.085.

When the graph amount used by the prognosis prediction system 100 is only the 10th graph feature, a value of the edge threshold value may be 30 HU. In such a case, according to an experiment using the test data of the 91 cases above, the C-index of the prognosis prediction system 100 was 0.643. In such a case, according to the experiment using the test data of the 91 cases above, a p value in the Log-rank test of the prognosis prediction system 100 was 0.256, and a p value in the Kaplan-Meier curve of the prognosis prediction system 100 was 0.005.

When the graph amount used by the prognosis prediction system 100 is only the 12th graph feature, a value of the edge threshold value may be 30 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.165, and a p value in the Kaplan-Meier curve of the prognosis prediction system 100 was 0.009.

When the graph amount used by the prognosis prediction system 100 is only the 11th graph feature, a value of the edge threshold value may be 30 HU. In such a case, according to an experiment using the test data of the 91 cases above, the C-index of the prognosis prediction system 100 was 0.636. In such a case, according to the experiment using the test data of the 91 cases above, a p value in the Log-rank test of the prognosis prediction system 100 was 0.165, and a p value in the Kaplan-Meier curve of the prognosis prediction system 100 was 0.006.

When the graph amount used by the prognosis prediction system 100 is only the 10th graph feature, a value of the edge threshold value may be 35 HU. In such a case, according to an experiment using the test data of the 91 cases above, the C-index of the prognosis prediction system 100 was 0.649. In such a case, according to the experiment using the test data of the 91 cases above, a p value in the Log-rank test of the prognosis prediction system 100 was 0.211, and a p value in the Kaplan-Meier curve of the prognosis prediction system 100 was 0.015.

When the graph amount used by the prognosis prediction system 100 is only the 12th graph feature, a value of the edge threshold value may be 35 HU. In such a case, according to an experiment using the test data of the 91 cases above, the C-index of the prognosis prediction system 100 was 0.641. In such a case, according to the experiment using the test data of the 91 cases above, a p value in the Log-rank test of the prognosis prediction system 100 was 0.181, and a p value in the Kaplan-Meier curve of the prognosis prediction system 100 was 0.048.

When the graph amount used by the prognosis prediction system 100 is only the 11th graph feature, a value of the edge threshold value may be 35 HU. In such a case, according to an experiment using the test data of the 91 cases above, the C-index of the prognosis prediction system 100 was 0.643. In such a case, according to the experiment using the test data of the 91 cases above, a p value in the Log-rank test of the prognosis prediction system 100 was 0.139, and a p value in the Kaplan-Meier curve of the prognosis prediction system 100 was 0.005.

When the graph amount used by the prognosis prediction system 100 is only the 10th graph feature, a value of the edge threshold value may be 40 HU. In such a case, according to an experiment using the test data of the 91 cases above, the C-index of the prognosis prediction system 100 was 0.650. In such a case, according to the experiment using the test data of the 91 cases above, a p value in the Log-rank test of the prognosis prediction system 100 was 0.204, and a p value in the Kaplan-Meier curve of the prognosis prediction system 100 was 0.015.

When the graph amount used by the prognosis prediction system 100 is only the 12th graph feature, a value of the edge threshold value may be 40 HU. In such a case, according to an experiment using the test data of the 91 cases above, the C-index of the prognosis prediction system 100 was 0.641. In such a case, according to the experiment using the test data of the 91 cases above, a p value in the Log-rank test of the prognosis prediction system 100 was 0.164, and a p value in the Kaplan-Meier curve of the prognosis prediction system 100 was 0.050.

When the graph amount used by the prognosis prediction system 100 is only the 11th graph feature, a value of the edge threshold value may be 40 HU. In such a case, according to an experiment using the test data of the 91 cases above, the C-index of the prognosis prediction system 100 was 0.649. In such a case, according to the experiment using the test data of the 91 cases above, a p value in the Log-rank test of the prognosis prediction system 100 was 0.131, and a p value in the Kaplan-Meier curve of the prognosis prediction system 100 was 0.015.

When the graph amount used by the prognosis prediction system 100 is only the 10th graph feature, a value of the edge threshold value may be 45 HU. In such a case, according to an experiment using the test data of the 91 cases above, the C-index of the prognosis prediction system 100 was 0.646. In such a case, according to the experiment using the test data of the 91 cases above, a p value in the Log-rank test of the prognosis prediction system 100 was 0.217, and a p value in the Kaplan-Meier curve of the prognosis prediction system 100 was 0.015.

When the graph amount used by the prognosis prediction system 100 is only the 12th graph feature, a value of the edge threshold value may be 45 HU. In such a case, according to an experiment using the test data of the 91 cases above, the C-index of the prognosis prediction system 100 was 0.640. In such a case, according to the experiment using the test data of the 91 cases above, a p value in the Log-rank test of the prognosis prediction system 100 was 0.165, and a p value in the Kaplan-Meier curve of the prognosis prediction system 100 was 0.039.

When the graph amount used by the prognosis prediction system 100 is only the 11th graph feature, a value of the edge threshold value may be 45 HU. In such a case, according to an experiment using the test data of the 91 cases above, the C-index of the prognosis prediction system 100 was 0.649. In such a case, according to the experiment using the test data of the 91 cases above, a p value in the Log-rank test of the prognosis prediction system 100 was 0.146, and a p value in the Kaplan-Meier curve of the prognosis prediction system 100 was 0.015.

When the graph amount used by the prognosis prediction system 100 is only the 10th graph feature, a value of the edge threshold value may be 50 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.260, and a p value in the Kaplan-Meier curve of the prognosis prediction system 100 was 0.017.

When the graph amount used by the prognosis prediction system 100 is only the 12th graph feature, a value of the edge threshold value may be 50 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.156, and a p value in the Kaplan-Meier curve of the prognosis prediction system 100 was 0.039.

When the graph amount used by the prognosis prediction system 100 is only the 11th graph feature, a value of the edge threshold value may be 50 HU. In such a case, according to an experiment using the test data of the 91 cases above, the C-index of the prognosis prediction system 100 was 0.642. In such a case, according to the experiment using the test data of the 91 cases above, a p value in the Log-rank test of the prognosis prediction system 100 was 0.185, and a p value in the Kaplan-Meier curve of the prognosis prediction system 100 was 0.015.

Hereinafter, an 18th graph feature in which each element in the second-type individual graph amount is the 2nd graph feature and the slope is the slope of the first-order term is referred to as the (18-1)th graph feature. Hereinafter, a 19th graph feature in which each element in the second-type individual graph amount is the 2nd graph feature is referred to as the (19-1)th graph feature. The slope of the first-order term is a slope of a term of a linear function of a function obtained when a histogram created based on the graph amount is approximated by a polynomial of a cubic function. In the histogram, a vertical axis represents a value of the graph amount, and a horizontal axis represents the edge threshold value.

The graph amount used by the prognosis prediction system 100 may be only the (18-1)th graph feature. In such a case, when the number of edge threshold values is 50, according to an experiment using the test data of the 91 cases above, the C-index of the prognosis prediction system 100 was 0.683. In such a case, when the number of edge threshold values is 50, according to the experiment using the test data of the 91 cases above, a p value in the Log-rank test of the prognosis prediction system 100 was 0.001, and a p value in the Kaplan-Meier curve of the prognosis prediction system 100 was 0.002.

The graph amount used by the prognosis prediction system 100 may be only the (19-1)th graph feature. In such a case, when the number of edge threshold values is 50, according to an experiment using the test data of the 91 cases above, the C-index of the prognosis prediction system 100 was 0.617. In such a case, when the number of edge threshold values is 50, according to the experiment using the test data of the 91 cases above, a p value in the Log-rank test of the prognosis prediction system 100 was 0.005, and a p value in the Kaplan-Meier curve of the prognosis prediction system 100 was 0.095.

Hereinafter, an 18th graph feature in which each element in the second-type individual graph amount is the 7th graph feature and the slope is the slope of the first-order term is referred to as the (18-2)th graph feature. Hereinafter, a 19th graph feature in which each element in the second-type individual graph amount is the 7th graph feature is referred to as the (19-2)th graph feature. Hereinafter, a 19th graph feature in which each element in the second-type individual graph amount is the 6th graph feature is referred to as the (19-3)th graph feature.

The graph amount used by the prognosis prediction system 100 may be only the (18-2)th graph feature. In such a case, when the number of edge threshold values is 50, according to an experiment using the test data of the 91 cases above, the C-index of the prognosis prediction system 100 was 0.682. In such a case, when the number of edge threshold values is 50, according to the experiment using the test data of the 91 cases above, a p value in the Log-rank test of the prognosis prediction system 100 was 0.001, and a p value in the Kaplan-Meier curve of the prognosis prediction system 100 was 0.004.

The graph amount used by the prognosis prediction system 100 may be only the (19-2)th graph feature. In such a case, when the number of edge threshold values is 50, according to an experiment using the test data of the 91 cases above, the C-index of the prognosis prediction system 100 was 0.600. In such a case, when the number of edge threshold values is 50, according to the experiment using the test data of the 91 cases above, a p value in the Log-rank test of the prognosis prediction system 100 was 0.007, and a p value in the Kaplan-Meier curve of the prognosis prediction system 100 was 0.282.

The graph amount used by the prognosis prediction system 100 may be only the (19-3)th graph feature. In such a case, when the number of edge threshold values is 50, according to an experiment using the test data of the 91 cases above, the C-index of the prognosis prediction system 100 was 0.682. In such a case, when the number of edge threshold values is 50, according to the experiment using the test data of the 91 cases above, a p value in the Log-rank test of the prognosis prediction system 100 was 0.000, and a p value in the Kaplan-Meier curve of the prognosis prediction system 100 was 0.008.

Hereinafter, an 18th graph feature in which each element in the second-type individual graph amount is the 4th graph feature and the slope is the slope of the first-order term is referred to as the (18-3)th graph feature. Hereinafter, a 19th graph feature in which each element in the second-type individual graph amount is the 4th graph feature is referred to as the (19-4)th graph feature.

The graph amount used by the prognosis prediction system 100 may be only the (18-3)th graph feature. In such a case, when the number of edge threshold values is 50, according to an experiment using the test data of the 91 cases above, the C-index of the prognosis prediction system 100 was 0.623. In such a case, when the number of edge threshold values is 50, according to the experiment using the test data of the 91 cases above, a p value in the Log-rank test of the prognosis prediction system 100 was 0.269, and a p value in the Kaplan-Meier curve of the prognosis prediction system 100 was 0.093.

The graph amount used by the prognosis prediction system 100 may be only the (19-4)th graph feature. In such a case, when the number of edge threshold values is 50, according to an experiment using the test data of the 91 cases above, the C-index of the prognosis prediction system 100 was 0.650. In such a case, when the number of edge threshold values is 50, according to the experiment using the test data of the 91 cases above, a p value in the Log-rank test of the prognosis prediction system 100 was 0.134, and a p value in the Kaplan-Meier curve of the prognosis prediction system 100 was 0.059.

Hereinafter, an 18th graph feature in which each element in the second-type individual graph amount is the 3rd graph feature and the slope is the slope of the third-order term is referred to as the (18-4)th graph feature. Hereinafter, an 18th graph feature in which each element in the second-type individual graph amount is the 3rd graph feature and the slope is the slope of the second-order term is referred to as the (18-5)th graph feature. Hereinafter, a 19th graph feature in which each element in the second-type individual graph amount is the 3rd graph feature is referred to as the (19-5)th graph feature.

The slope of the third-order term is a slope of a term of a cubic function of a function obtained when a histogram created based on the graph amount is approximated by a polynomial of a cubic function. The slope of the second-order term is a slope of a term of a quadratic function of a function obtained when a histogram created based on the graph amount is approximated by a polynomial of a cubic function.

The graph amount used by the prognosis prediction system 100 may be only the (18-4)th graph feature. In such a case, when the number of edge threshold values is 50, according to an experiment using the test data of the 91 cases above, the C-index of the prognosis prediction system 100 was 0.541. In such a case, when the number of edge threshold values is 50, according to the experiment using the test data of the 91 cases above, a p value in the Log-rank test of the prognosis prediction system 100 was 0.322, and a p value in the Kaplan-Meier curve of the prognosis prediction system 100 was 0.678.

The graph amount used by the prognosis prediction system 100 may be only the (18-5)th graph feature. In such a case, when the number of edge threshold values is 50, according to an experiment using the test data of the 91 cases above, the C-index of the prognosis prediction system 100 was 0.612. In such a case, when the number of edge threshold values is 50, according to the experiment using the test data of the 91 cases above, a p value in the Log-rank test of the prognosis prediction system 100 was 0.018, and a p value in the Kaplan-Meier curve of the prognosis prediction system 100 was 0.137.

The graph amount used by the prognosis prediction system 100 may be only the (19-5)th graph feature. In such a case, when the number of edge threshold values is 50, according to an experiment using the test data of the 91 cases above, the C-index of the prognosis prediction system 100 was 0.428. In such a case, when the number of edge threshold values is 50, according to the experiment using the test data of the 91 cases above, a p value in the Log-rank test of the prognosis prediction system 100 was 0.218, and a p value in the Kaplan-Meier curve of the prognosis prediction system 100 was 0.595.

Hereinafter, an 18th graph feature in which each element in the second-type individual graph amount is the 9th graph feature and the slope is the slope of the first-order term is referred to as the (18-6)th graph feature. Hereinafter, a 19th graph feature in which each element in the second-type individual graph amount is the 9th graph feature is referred to as the (19-6)th graph feature.

The graph amount used by the prognosis prediction system 100 may be only the (18-6)th graph feature. In such a case, when the number of edge threshold values is 50, according to an experiment using the test data of the 91 cases above, the C-index of the prognosis prediction system 100 was 0.592. In such a case, when the number of edge threshold values is 50, according to the experiment using the test data of the 91 cases above, a p value in the Log-rank test of the prognosis prediction system 100 was 0.121, and a p value in the Kaplan-Meier curve of the prognosis prediction system 100 was 0.426.

The graph amount used by the prognosis prediction system 100 may be only the (19-6)th graph feature. In such a case, when the number of edge threshold values is 50, according to an experiment using the test data of the 91 cases above, the C-index of the prognosis prediction system 100 was 0.627. In such a case, when the number of edge threshold values is 50, according to the experiment using the test data of the 91 cases above, a p value in the Log-rank test of the prognosis prediction system 100 was 0.051, and a p value in the Kaplan-Meier curve of the prognosis prediction system 100 was 0.096.

Hereinafter, an 18th graph feature in which each element in the second-type individual graph amount is the 8th graph feature and the slope is the slope of the first-order term is referred to as the (18-7)th graph feature. Hereinafter, a 19th graph feature in which each element in the second-type individual graph amount is the 8th graph feature is referred to as the (19-7)th graph feature.

The graph amount used by the prognosis prediction system 100 may be only the (18-7)th graph feature. In such a case, when the number of edge threshold values is 50, according to an experiment using the test data of the 91 cases above, the C-index of the prognosis prediction system 100 was 0.683. In such a case, when the number of edge threshold values is 50, according to the experiment using the test data of the 91 cases above, a p value in the Log-rank test of the prognosis prediction system 100 was 0.001, and a p value in the Kaplan-Meier curve of the prognosis prediction system 100 was 0.002.

The graph amount used by the prognosis prediction system 100 may be only the (19-7)th graph feature. In such a case, when the number of edge threshold values is 50, according to an experiment using the test data of the 91 cases above, the C-index of the prognosis prediction system 100 was 0.617. In such a case, when the number of edge threshold values is 50, according to the experiment using the test data of the 91 cases above, a p value in the Log-rank test of the prognosis prediction system 100 was 0.005, and a p value in the Kaplan-Meier curve of the prognosis prediction system 100 was 0.095.

Hereinafter, an 18th graph feature in which each element in the second-type individual graph amount is the 10th graph feature and the slope is the slope of the third-order term is referred to as the (18-8)th graph feature. Hereinafter, an 18th graph feature in which each element in the second-type individual graph amount is the 10th graph feature and the slope is the slope of the second-order term is referred to as the (18-9)th graph feature. Hereinafter, an 18th graph feature in which each element in the second-type individual graph amount is the 10th graph feature and the slope is the slope of the first-order term is referred to as the (18-10)th graph feature.

The graph amount used by the prognosis prediction system 100 may be only the (18-8)th graph feature. In such a case, when the number of edge threshold values is 50, according to an experiment using the test data of the 91 cases above, the C-index of the prognosis prediction system 100 was 0.653. In such a case, when the number of edge threshold values is 50, according to the experiment using the test data of the 91 cases above, a p value in the Log-rank test of the prognosis prediction system 100 was 0.002, and a p value in the Kaplan-Meier curve of the prognosis prediction system 100 was 0.046.

The graph amount used by the prognosis prediction system 100 may be only the (18-9)th graph feature. In such a case, when the number of edge threshold values is 50, according to an experiment using the test data of the 91 cases above, the C-index of the prognosis prediction system 100 was 0.637. In such a case, when the number of edge threshold values is 50, according to the experiment using the test data of the 91 cases above, a p value in the Log-rank test of the prognosis prediction system 100 was 0.004, and a p value in the Kaplan-Meier curve of the prognosis prediction system 100 was 0.064.

The graph amount used by the prognosis prediction system 100 may be only the (18-10)th graph feature. In such a case, when the number of edge threshold values is 50, according to an experiment using the test data of the 91 cases above, the C-index of the prognosis prediction system 100 was 0.581. In such a case, when the number of edge threshold values is 50, according to the experiment using the test data of the 91 cases above, a p value in the Log-rank test of the prognosis prediction system 100 was 0.034, and a p value in the Kaplan-Meier curve of the prognosis prediction system 100 was 0.223.

Hereinafter, a 19th graph feature in which each element in the second-type individual graph amount is the 10th graph feature is referred to as the (19-8)th graph feature. Hereinafter, a 19th graph feature in which each element in the second-type individual graph amount is the 12th graph feature is referred to as the (19-9)th graph feature.

The graph amount used by the prognosis prediction system 100 may be only the (19-8)th graph feature. In such a case, when the number of edge threshold values is 50, according to an experiment using the test data of the 91 cases above, the C-index of the prognosis prediction system 100 was 0.622. In such a case, when the number of edge threshold values is 50, according to the experiment using the test data of the 91 cases above, a p value in the Log-rank test of the prognosis prediction system 100 was 0.958, and a p value in the Kaplan-Meier curve of the prognosis prediction system 100 was 0.016.

The graph amount used by the prognosis prediction system 100 may be only the (19-9)th graph feature. In such a case, when the number of edge threshold values is 50, according to an experiment using the test data of the 91 cases above, the C-index of the prognosis prediction system 100 was 0.647. In such a case, when the number of edge threshold values is 50, according to the experiment using the test data of the 91 cases above, a p value in the Log-rank test of the prognosis prediction system 100 was 0.293, and a p value in the Kaplan-Meier curve of the prognosis prediction system 100 was 0.039.

Hereinafter, an 18th graph feature in which each element in the second-type individual graph amount is the 11th graph feature and the slope is the slope of the third-order term is referred to as the (18-11)th graph feature. Hereinafter, an 18th graph feature in which each element in the second-type individual graph amount is the 11th graph feature and the slope is the slope of the second-order term is referred to as the (18-12)th graph feature. Hereinafter, an 18th graph feature in which each element in the second-type individual graph amount is the 11th graph feature and the slope is the slope of the first-order term is referred to as the (18-13)th graph feature.

The graph amount used by the prognosis prediction system 100 may be only the (18-11)th graph feature. In such a case, when the number of edge threshold values is 50, according to an experiment using the test data of the 91 cases above, the C-index of the prognosis prediction system 100 was 0.576. In such a case, when the number of edge threshold values is 50, according to the experiment using the test data of the 91 cases above, a p value in the Log-rank test of the prognosis prediction system 100 was 0.216, and a p value in the Kaplan-Meier curve of the prognosis prediction system 100 was 0.336.

The graph amount used by the prognosis prediction system 100 may be only the (18-12)th graph feature. In such a case, when the number of edge threshold values is 50, according to an experiment using the test data of the 91 cases above, the C-index of the prognosis prediction system 100 was 0.533. In such a case, when the number of edge threshold values is 50, according to the experiment using the test data of the 91 cases above, a p value in the Log-rank test of the prognosis prediction system 100 was 0.973, and a p value in the Kaplan-Meier curve of the prognosis prediction system 100 was 0.439.

The graph amount used by the prognosis prediction system 100 may be only the (18-13)th graph feature. In such a case, when the number of edge threshold values is 50, according to an experiment using the test data of the 91 cases above, the C-index of the prognosis prediction system 100 was 0.599. In such a case, when the number of edge threshold values is 50, according to the experiment using the test data of the 91 cases above, a p value in the Log-rank test of the prognosis prediction system 100 was 0.008, and a p value in the Kaplan-Meier curve of the prognosis prediction system 100 was 0.042.

Hereinafter, a 19th graph feature in which each element in the second-type individual graph amount is the 11th graph feature is referred to as the (19-10)th graph feature. Hereinafter, a 20th graph feature in which each element in the second-type individual graph amount is the 10th graph feature is referred to as a (20-1)th graph feature. Hereinafter, a 21th graph feature in which each element in the second-type individual graph amount is the 10th graph feature is referred to as a (21-1)th graph feature.

The graph amount used by the prognosis prediction system 100 may be only the (19-10)th graph feature. In such a case, when the number of edge threshold values is 50, according to an experiment using the test data of the 91 cases above, the C-index of the prognosis prediction system 100 was 0.665. In such a case, when the number of edge threshold values is 50, according to the experiment using the test data of the 91 cases above, a p value in the Log-rank test of the prognosis prediction system 100 was 0.002, and a p value in the Kaplan-Meier curve of the prognosis prediction system 100 was 0.001.

The graph amount used by the prognosis prediction system 100 may be only the (20-1)th graph feature. In such a case, when the number of edge threshold values is 50, according to an experiment using the test data of the 91 cases above, the C-index of the prognosis prediction system 100 was 0.618. In such a case, when the number of edge threshold values is 50, according to the experiment using the test data of the 91 cases above, a p value in the Log-rank test of the prognosis prediction system 100 was 0.808, and a p value in the Kaplan-Meier curve of the prognosis prediction system 100 was 0.079.

The graph amount used by the prognosis prediction system 100 may be only the (21-1)th graph feature. In such a case, when the number of edge threshold values is 50, according to an experiment using the test data of the 91 cases above, the C-index of the prognosis prediction system 100 was 0.577. In such a case, when the number of edge threshold values is 50, according to the experiment using the test data of the 91 cases above, a p value in the Log-rank test of the prognosis prediction system 100 was 0.958, and a p value in the Kaplan-Meier curve of the prognosis prediction system 100 was 0.716.

The prognosis prediction information acquisition device 1 does not necessarily need to execute the training data set generation processing. In such a case, the training data set, instead of the unprocessed training data set, is input to the prognosis prediction information acquisition device 1. In such a case, the training data set acquisition unit 104 executes processing of acquiring the training data set input to the communication unit 12 or the input unit 13 instead of processing of generating the training data set based on the unprocessed training data set. When the training data set is recorded in the storage unit 14 in advance, the training data set acquisition unit 104 may acquire the training data set by reading the training data set from the storage unit 14.

The prognosis prediction device 2 does not necessarily need to execute preprocessing. In such a case, the graph tumor information, instead of the tumor image data, is input to the prognosis prediction device 2. In such a case, the input data acquisition unit 240 acquires graph tumor information instead of acquiring tumor image data. When the input data acquisition unit 240 acquires the graph tumor information, the prognosis prediction unit 250 executes the main processing without executing the preprocessing. When the graph tumor information has been recorded in the storage unit 24 in advance, the input data acquisition unit 240 may acquire the graph tumor information by reading the graph tumor information from the storage unit 24.

The prognosis prediction information acquisition device 1 may be implemented using a plurality of information processing devices communicably connected via a network. In this case, the functional units in the prognosis prediction information acquisition device 1 may be implemented in the plurality of information processing devices in a distributed manner.

The prognosis prediction device 2 may be implemented using a plurality of information processing devices communicably connected via a network. In this case, the functional units in the prognosis prediction device 2 may be implemented in the plurality of information processing devices in a distributed manner.

The prognosis prediction information acquisition device 1 and the prognosis prediction device 2 need not necessarily be implemented as different devices. The prognosis prediction information acquisition device 1 and the prognosis prediction device 2 may be implemented as one device.

The prognosis prediction system 100 may be implemented using a plurality of information processing devices communicably connected via a network. In this case, functional units in the prognosis prediction system 100 may be implemented in the plurality of information processing devices in a distributed manner.

All or a part of functions of the prognosis prediction system 100 may be implemented using hardware such as an application specific integrated circuit (ASIC), a programmable logic device (PLD), and a field programmable gate array (FPGA). The program can be recorded in a computer-readable recording medium. The computer-readable recording medium refers to a storage device such as a portable medium such as a flexible disk, a magneto-optical disk, a ROM, and a CD-ROM, and a hard disk built in a computer system. The program may be transmitted via a telecommunication line.

Although the embodiment of the invention has been described in detail with reference to the drawings, the specific configuration is not limited to the embodiment, and a design or the like within a scope not departing from the gist of the invention is also included.

REFERENCE SIGNS LIST

100: prognosis prediction system
1: prognosis prediction information acquisition device
2: prognosis prediction device
11: control unit
12: communication unit
13: input unit
14: storage unit
15: output unit
101: communication control unit
102: input control unit
103: output control unit
104: training data set acquisition unit
105: model execution unit
106: update unit
107: end determination unit
108: storage control unit
21: control unit
22: communication unit
23: input unit
24: storage unit
25: output unit
210: communication control unit
220: input control unit
230: output control unit
240: input data acquisition unit
250: prognosis prediction unit
251: preprocessing execution unit
252: main processing execution unit
260: storage control unit
91: processor
92: memory
93: processor
94: memory

The invention claimed is:

1. A prognosis prediction device comprising:
a processor; and
a storage medium having computer program instructions stored thereon, wherein the computer program instructions, when executed by the processor, perform processing of:

predicting, using prognosis prediction information that indicates a relationship between graph tumor information that is information on an image of a tumor represented using an amount defined by a graph theory and a prognosis of a person or an animal having the tumor, a prognosis of an estimation target based on graph tumor information indicating an image of a tumor of the estimation target, and
wherein
the amount defined by the graph theory is an amount related to a vertex of a graph,
the vertex of the graph is defined for each unit pixel that is a collection of one or more pixels adjacent to each other,
the amount related to the vertex of the graph is an amount indicating a positional relationship between vertices for which weights are defined and a weight of each vertex, and
the weight is a predefined index value related to a pixel value of each pixel in the unit pixel.

2. The prognosis prediction device according to claim 1, wherein
the amount defined by the graph theory is an amount related to an edge of a graph.

3. The prognosis prediction device according to claim 1, wherein
the amount defined by the graph theory is an amount related to a degree of a graph.

4. The prognosis prediction device according to claim 1, wherein
the amount defined by the graph theory is an amount related to a minimum spanning tree of a graph.

5. A non-transitory computer readable medium which stores a program for causing a computer to function as the prognosis prediction device according to claim 1.

6. A prognosis prediction method comprising:
predicting, using prognosis prediction information that indicates a relationship between graph tumor information that is information on an image of a tumor represented using an amount defined by a graph theory and a prognosis of a person or an animal having the tumor, a prognosis of an estimation target based on graph tumor information indicating an image of a tumor of the estimation target, wherein the amount defined by the graph theory is an amount related to a vertex of a graph, wherein the vertex of the graph is defined for each unit pixel that is a collection of one or more pixels adjacent to each other, wherein the amount related to the vertex of the graph is an amount indicating a positional relationship between vertices for which weights are defined and a weight of each vertex, and wherein the weight is a predefined index value related to a pixel value of each pixel in the unit pixel.

* * * * *